United States Patent [19]

Malins

[11] Patent Number: 5,945,675
[45] Date of Patent: Aug. 31, 1999

[54] METHODS OF SCREENING FOR A TUMOR OR TUMOR PROGRESSION TO THE METASTATIC STATE

[75] Inventor: Donald C. Malins, Seattle, Wash.

[73] Assignee: Pacific Northwest Research Foundation, Seattle, Wash.

[21] Appl. No.: 08/819,144

[22] Filed: Mar. 17, 1997

Related U.S. Application Data

[60] Provisional application No. 60/035,757, Jan. 6, 1997, provisional application No. 60/018,867, May 28, 1996, and provisional application No. 60/014,708, Mar. 18, 1996.

[51] Int. Cl.$^6$ .............................. A61B 6/00; G01N 21/35
[52] U.S. Cl. ................................ 250/339.12; 250/339.08
[58] Field of Search ........................... 250/339.08, 339.12

[56] References Cited

U.S. PATENT DOCUMENTS

| 5,435,309 | 7/1995 | Thomas et al. . | |
|---|---|---|---|
| 5,596,992 | 1/1997 | Haaland et al. | 600/473 |

FOREIGN PATENT DOCUMENTS

WO 91/11701  8/1991  WIPO .
WO 95/26502  10/1995 WIPO .

OTHER PUBLICATIONS

Malins et al., "The Etiology and Prediction of Breast Cancer," *Cancer* 75(2): 503–517, Jan. 1995.

Malins et al., "Progression of human breast cancers to the metastatic state is linked to hydroxyl radical–induced DNA damage," *Proc. Natl. Acad. Sci. USA* 93: 2557–2563, Mar. 1996.

Malins et al., "Tumor progression to the metastatic state involves structural modifications in DNA markedly different from those associated with primary tumor formation," *Proc. Natl. Acad. Sci. USA* 93: 14047–14052, Nov. 1996.

*Primary Examiner*—Constantine Hannaher
*Attorney, Agent, or Firm*—Seed and Berry LLP

[57] ABSTRACT

Methods of screening for a tumor or tumor progression to the metastatic state are a provided. The screening methods are based on the characterization of DNA by principal components analysis of spectral data yielded by Fourier transform-infrared spectroscopy of DNA samples. The methods are applicable to a wide variety of DNA samples and cancer types.

5 Claims, 19 Drawing Sheets

*BASED ON LOGISTIC REGRESSION MODEL USING THE 1ST SIX FACTORS FROM FACTOR ANALYSIS

METHODS OF SCREENING FOR A TUMOR OR TUMOR PROGRESSION TO THE METASTATIC STATE

CROSS-REFERENCE TO RELATED APPLICATIONS

This Application claims the benefit of U.S. Provisional Application No. 60/035,757, filed Jan. 6, 1997, filed May 28, 1996, and U.S. Provisional Application No. 60/014,708, filed Mar. 18, 1996.

TECHNICAL FIELD

The present invention is generally directed toward screening for a tumor or progression of a tumor to the metastatic state. The invention is more particularly related to characterizing DNA based upon principal components analysis of spectral data yielded by Fourier transform-infrared spectroscopy of DNA samples.

BACKGROUND OF THE INVENTION

Despite enormous expenditures of both financial and human resources over the last twenty-five plus years, the detection of new tumors or the recurrence of tumors remains an unfulfilled goal of humankind. Particularly frustrating is the fact that a number of cancers are treatable if detected at an early stage, but go undetected in many patients for lack of a reliable screening procedure. In addition, the need is acute for reliable screening procedures that discriminate non-metastatic primary tumors (or non-cancerous disease states) from metastatic tumors, or are predictive of progression to the metastatic state. Metastasis of tumors is a major cause of treatment failure in cancer patients. It is a complex process involving the detachment of cells from the primary neoplasm, their entrance into the circulation, and the eventual colonization of local and distant tissue sites.

Frequently, physicians must err on the side of caution, and request that a patient undergo surgical or other procedures that dramatically affects the patient's quality of life, without identification of the disease state as a tumor with a propensity to progress to the metastatic state. For illustrative purposes, two particular cancers, prostate and breast cancers, are described in more detail and are representative of cancers in need of new approaches, which the invention disclosed herein provides.

Prostate cancer is a leading cause of death in men. Thus, there is a keen interest in the etiology of this disease, as well as in the development of techniques for predicting its occurrence at early stages of oncogenesis. Little is known about the etiology of prostate cancer, the most prevalent form being adenocarcinoma. However, several studies have focused on inactivation of the tumor suppressor gene TP53 and altered DNA methylation patterns as possible factors. In addition, free radicals, arising from redox cycling of hormones, have recently been implicated in prostate cancer. This is consistent with evidence showing that the hydroxyl radical (•OH) produces mutagenic alterations in DNA, such as 8-hydroxyguanine (8-OH-Gua) and 8-hydroxyadenine (8-OH-Ade), that have been linked to carcinogenesis in a variety of studies. Despite these findings, virtually no understanding exists of the possible relationship between the •OH-modification of DNA and prostate cancer.

Prostate tissue may contain areas of benign prostatic hyperplasia (BPH), which is not regarded as a pre-malignant lesion, although it often accompanies prostate cancer. The etiology of BPH is unknown, as is its relationship to prostate cancer. Due to the difficulties in the current approaches to the diagnosis of prostate cancer, there is a need in the art for improved methods. The present invention fulfills this need, and further provides other related advantages.

Breast cancer is a leading cause of death in women and is the most common malignancy in women. The incidence for developing breast cancer is on the rise. One in nine women will be diagnosed with the disease. Standard approaches to treat breast cancer have centered around a combination of surgery, radiation and chemotherapy. In certain malignancies, these approaches have been successful and have effected a cure. However, when diagnosis is beyond a certain stage, breast cancer is most often incurable. Invasive ductal carcinoma is a common form of breast cancer which can metastasize. Alternative approaches to early detection are needed. Due to the difficulties in the current approaches to the diagnosis of breast cancer, there is a need in the art for improved methods. The present invention fulfills this need, and further provides other related advantages.

SUMMARY OF THE INVENTION

Briefly stated, the present invention provides methods of screening for a tumor or tumor progression to the metastatic state, and methods of assessing the genotoxicity of an environment. The invention is applicable to a wide variety of DNA samples and cancers, and to a wide variety of genotoxic enviromnents.

In one aspect, the present invention provides a method of screening for a tumor or tumor progression to the metastatic state comprising the steps of: (a) subjecting a DNA sample to Fourier transform-infrared (FT-IR) spectroscopy to produce FT-IR spectral data; (b) analyzing the FT-IR spectral data of step (a) by principal components analysis (PCA); and (c) comparing the PCA of step (b) to the PCA of FT-IR spectra for DNA samples from non-cancerous, non-metastatic tumor or metastatic tumor samples.

In another aspect, the present invention provides a method for assessing the genotoxicity of an environment comprising the steps of: (a) subjecting a DNA sample of a first organism in an environment to Fourier transform-infrared (FT-IR) spectroscopy to produce FT-IR spectral data; (b) analyzing the FT-IR spectral data of step (a) by principal components analysis (PCA); and (c) comparing the PCA of step (b) to the PCA of FT-IR spectra for DNA samples of: (1) the first organism prior to introduction in the environment of step (a), or (2) a second organism in a nonpolluted environment.

These and other aspects of the present invention will become evident upon reference to the following detailed description and attached drawings.

DETAILED DESCRIPTION OF THE INVENTION

Figure 1:
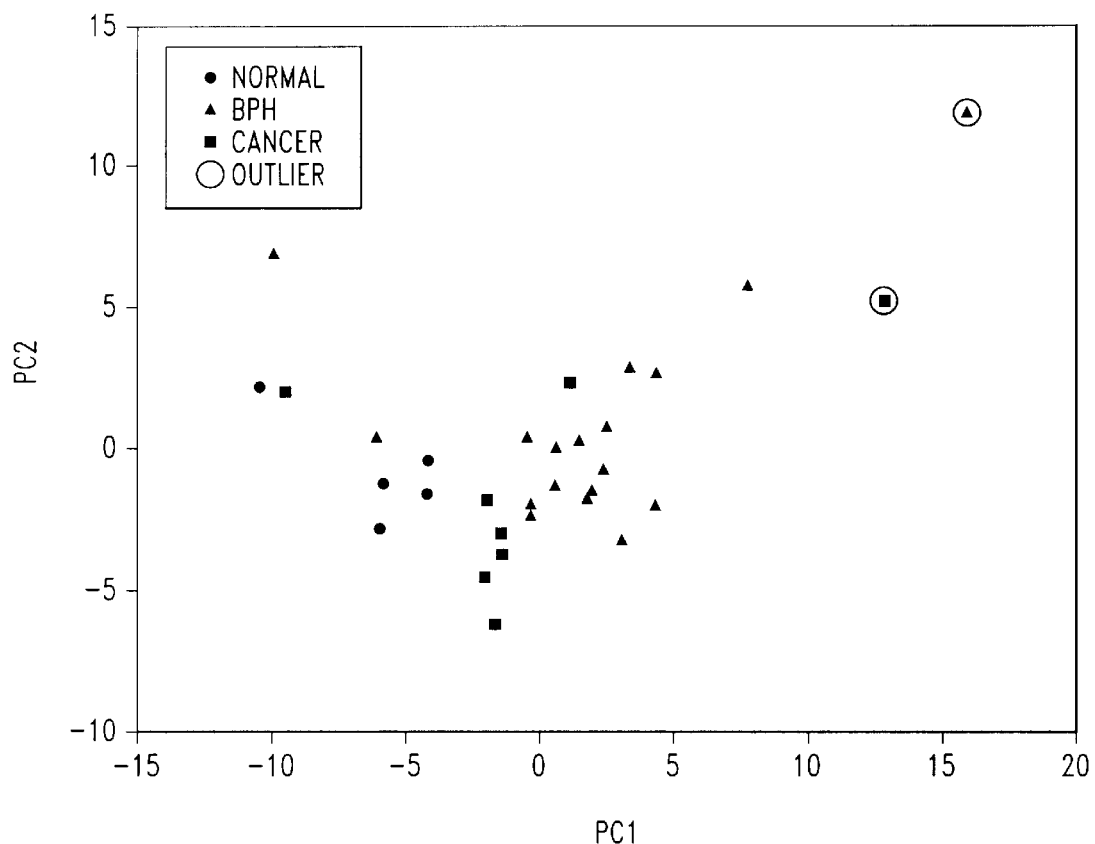
FIG. 1 shows a two-dimensional PC plot derived by PCA/FT-IR spectral analysis showing distinct clustering of normal, benign prostatic hyperplasia ("BPH") and prostate cancer points. Notably, both of the groups of prostate lesions occur to the right of the points for the DNA of normal prostate.

As noted above, the present invention is directed, in one aspect, toward methods of screening for a tumor or tumor progression to the metastatic state. The methods are based on the analysis of DNA. Because DNA is ubiquitous in all organisms, the methods of the invention are not limited to use of a particular DNA sample. Thus, a wide variety of cancers may be screened. Representative examples of cancers include breast, urogenital, melanoma, liver, renal, pancreatic, lung, circulation system, nervous system or colorectal cancers. Urogenital cancers include prostate, cervical, ovarian, bladder or endometrial cancers. Circulation system cancers include lymphomas. Nervous system cancers include brain cancers.

As used herein, the term "screening for" includes detecting, monitoring, diagnosing or prognosticating (predicting). DNA is analyzed as described herein to screen for a tumor. As used herein, "a tumor" may be present for the first time, or reoccurring, or in the process of occurring or reoccurring. The last scenarios (i.e., process of) represent opportunities for assessing, and insight into, the risk of cancer prior to clinical manifestation. The present invention may be used to predict that cancer cells are likely to form, even though they have yet to appear based on currently available methodologies. DNA is also analyzed as described he-rein to screen for tumor progression to the metastatic state. Progression of the tumor to the metastatic state refers to the end point (i.e., the metastatic state) as well as any intermediate point on the way to the end point.

A "DNA samples" is DNA in, or from, any source. DNA may be removed from a variety of sources, including a tissue source or a fluid source. Tissue sources include tissue from an organ or membrane or skin. Fluid sources include whole blood, serum, plasma, urine, synovial, saliva, sputum, cerebrospinal fluid, or fractions thereof. With respect to a tissue sample, for example, tissue may be removed from an organism by biopsy (such as a fine needle biopsy) and the DNA extracted, all by techniques well known to those in the art. Similarly DNA may be extracted from a fluid source using known techniques. Although extraction/isolation of DNA may be preferred, DNA need not be extracted/isolated in order to carry out the invention. It is possible to examine DNA directly using Fourier transform-infrared (FT-IR) spectroscopy. For example, by specifically limiting the IR scan to cellular nuclei, spectral profiles of high concentration may be generated. Therefore, a DNA sample may be extracted/isolated DNA or a sample may include DNA.

It is possible to store tissue for later analysis of the DNA. For example, excised tissue may be frozen immediately in liquid nitrogen and maintained at −80° C. Following isolation of the DNA from such tissue, it is normally dissolved in deionized water and aliquoted into portions for FT-IR spectroscopy. Aliquots are typically dried completely by lyophilization, purged with pure nitrogen and stored in an evacuated, sealed glass vial.

Within the present invention a DNA sample is subjected to FT-IR spectroscopy and the FT-IR spectral data analyzed by principal components analysis. The starting point for the characterization of DNA in a sample is a set of IR spectra. Each spectrum shows numerical absorbances at each integer wavenumber, i.e., generally from 4000–700 $cm^{-1}$ and typically from 2000–700 $cm^{-1}$. Infrared (IR) spectra of DNA samples are obtained with a Fourier Transform-IR spectrometer, for example a Perkin-Elmer System 2000 (The Perkin-Elmer Corp., Norwalk, Conn.) equipped with an IR microscope and a wide-range mercury-cadmium-telluride detector. The DNA is generally placed on a barium fluoride plate in an atmosphere with a relative humidity of less than ~60% and flattened to make a transparent film. Using the IR microscope in a visual-observation mode, a uniform and transparent portion of the sample is selected to avoid a scattering or wedge effect in obtaining transmission spectra. Each analysis is generally performed in triplicate on 3–5 μg of DNA and the spectra were computer averaged. Generally, two hundred fifty-six scans at a 4-$cm^{-1}$ resolution are performed for each analysis to obtain spectra in a frequency range of 4000–700 $cm^{-1}$. Typically 3–5 minutes elapsed from when the glass vial is broken to when each IR spectrum is obtained. Typically, the DNA specimens vary in thickness, yielding a diverse set of absorbances or spectral intensities. None of the IR spectra show a 1703-$cm^{-1}$ band, which is indicative of specific base pairing. This fact indicates that the samples have acquired a disordered form, the D-configuration.

The IR spectra are obtained in transmission units and converted to absorbance units for data processing. For example, the Infrared Data Manager software package (The Perkin-Elmer Corp.) may be used to control the spectrometer and to obtain the IR spectra. Additionally the GRAMS/2000 software package (Galactic Industries Corp., Salem, N.H.) may be used perform postrun spectrographic data analysis. Each spectrum is converted to a spreadsheet format that includes a specific absorbance for every wavenumber from 4000 to 700 $cm^{-1}$.

In processing the IR data, a baseline adjustment is generally used for all spectra to remove the effect of background absorbance. In order to do this, the mean absorbance across 11 wavenumbers, centered at the lowest point (e.g., for the range 2000–700 $cm^{-1}$) is subtracted from absorbances at all frequencies. In addition, the IR data is generally normalized. Because there is not a well-established reference peak in the frequency range of 2000–700 $cm^{-1}$ useful for normalization, generally normalization is achieved by converting all absorbances to a constant mean intensity in the range of interest. For example, the region of 1750–700 $cm^{-1}$ (a span of 1051 wavenumbers) has been typically chosen within the present invention as the primary region for analysis, because it includes widely varying absorbances. After the removal of a baseline, described above, absorbances at all wavenumbers in a spectrum are divided by the mean absorbance ranging form 1750 to 700 $cm^{-1}$ for that spectrum, resulting in a mean spectral intensity of 1.0 for every specimen. All further analyses are generally performed on these baselined, normalized spectra (although analysis without the mean removed is also possible).

Within the present invention, factor analysis is used to study the variation among spectra and the relation of this variation to subgroups, such as cancer versus non-cancer. In particular, spectral data acquired by FT-IR spectroscopy are analyzed using a principal components analysis (PCA) statistical approach. PCA is a statistical procedure applied to a single set of variables with the purpose of revealing a few variables (principal component scores or PCs) that are independent of each other and that capture most of the information in the original long list of variables. (e.g., Timm. N. H. in *Multivalent Analysis*, ed. Timm, N. H., 1975. Brooks/Cole, Monterey, Calif., pp. 528–570). PCA yields a few PCs that summarize the major features that vary across spectra. For example, five principal components (i.e., five dimensions) can be sufficient to describe 1051 dimensions of FT-IR spectra (with the grand mean of all spectra subtracted from each spectrum) and visual representation in two or three dimensions is adequate. PCA is available in many basic and advanced statistical programs, such as SAS and S-Plus.

The entire analysis is generally carried out with core clusters from each of the three groups (DNA from non-cancerous samples, non-metastatic tumor samples, and metastatic tumor samples), although it is possible to use less than all three groups (e.g., two of three groups, or non-cancerous samples versus all tumor samples regardless of whether metastatic or not). Using cluster analysis, those members of a specified group that stood apart from others in the core group are identified. The isolated group members all stand apart from any others in their group at Euclidean distances generally representing at least a 12% difference in the mean normalized absorbance, a visibly notable difference when spectra are conventionally plotted. The core clusters can be considered to be the more commonly encountered DNA structural phenotypes, whereas the isolated group members represent less frequent phenotypes not present in great enough numbers to study with the sample, yet overly influential in the analysis if included.

The determination of whether DNA structural changes for the progression of non-cancerous (NC) to non-metastatic tumor (NMT) are the same as for the progression of non-metastatic tumor (NMT) to metastatic tumor (MT) is tested on the basis of centroids statistically derived from groups of points. The centroid is the vector of mean absorbances of the 1051 individual wavenumbers from 1750 to 700 $cm^{-1}$. If the two progressions are similar, then the centroids of the three groups line up in two- and three-dimensional space.

Formally, the hypothesis that $\cos(\theta)=1.0$ is tested, where $\theta$ is the angle between a vector x pointing from the NC to the NMT centroid and a vector y pointing from the NMT to the MT centroid. $\cos(\theta)$ is defined by $\cos(\theta)=xy/(|x|\cdot|y|)$. The vector x is indexed by wavenumbers and, at each wavenumber, contains the difference between the mean normalized absorbance of NMT spectra and the mean normalized absorbance of NC spectra. The vector y shows the corresponding difference for MT minus NMT spectra. An angle $\theta=0$ [which is equivalent to $\cos(\theta)=1.0$] implies that the MT is a "virtual straight ahead" continuation of the NC→NMT progression, and that the centroids line up, whereas $\theta\neq 0$ implies that the NMT→MT progression involves a different suite of spectral (structural) changes. The hypothesis that $\cos(\theta)=1.0$ is tested using the bootstrap method (Efron and Gong, *Am. Stat.* 37: 36–48, 1983), which involves resampling with replacement from the NC, NMT, and MT core clusters and calculation of $\cos(\theta)$ for each resampling.

To determine if the populations from which the NC and NMT core clusters are drawing have distinct centroids (i.e., distinct mean absorbance spectra), a permutation test is carried out on the distance between the NC and NMT centroids, randomly permuting labels among NC and NMT samples and recalculating distances between centroids. A similar permutation test is carried out for the distance between the NMT and MT centroids. Finally, the sizes of the three core clusters is compared using the Kruskal-Wallis ANOVA and Mann-Whitney (MW) tests on the distance of each spectrum to the centroid of its cluster. (The P values from the Kruskal-Wallis and MW tests are approximate, due to some statistical dependence introduced when sample values are compared with their sample mean.)

Wavenumber-absorbance relationships of infrared spectra of DNA analyzed by principal components analysis (i.e., PCA of FT-IR spectral data) may be expressed as points in space. Each point represents a highly discriminating measure of DNA structure. These PC scores can be plotted in 2- and 3-dimensional plots. The position of a spectrum in a plot is a description of how it differ, from or is similar to other spectra in the plot. Different plot symbols or clusters for different groups of spectra help to highlight clustering of spectra. In addition, when two groups of spectra are analyzed, logistic regression can be used to develop a model for classifying the spectra based on their PC scores. Logistic regression is a method commonly used for classification and is available in many statistical software packages (such as SAS and S-Plus). The PC scores are predictors and the result is an equation (a model) which can be used to classify specimens. Each specimen is tagged with a numerical probability of being in the cancer group (for example) versus the non-cancer group. The results of this analysis can be plotted as a sigmoid curve with the cancer risk; score (the logit of the estimated probability) on the X-axis and the estimated probability on the Y-axis using the prediction equation, the probability for a new specimen can also be calculated. By choosing a cut point (such as a probability of 0.5 or greater) all specimens can be classified as cancer or non-cancer (for example). The sensitivity and specificity of the classification can also be calculated using standard methods.

The present invention analyzes DNA samples by PCA of FT-IR spectral data and shows surprisingly that the direction of the progression of non-cancerous ("normal") DNA to non-metastatic tumor ("primary tumor") DNA differs significantly from the direction of the progression of primary tumor to metastatic tumor. By comparison of PCA of FT-IR spectra for a DNA sample of interest, to PCA of FT-IR spectra for DNA samples from known non-cancerous, non-metastatic tumor and metastatic tumor samples, one may determine whether the sample of interest is in one of these three states or progressing toward one of the tumor states.

For example, the present invention provides methods for the detection of prostate cancer. The present invention applies technology employing principal components analysis (PCA) of Fourier-transform infrared (FT-IR) spectroscopy (PCA/FT-IR technology) to DNA derived from the normal prostate, benign prostatic hyperplasia (BPH) and adenocarcinoma. As described in detail below, clusters of points representing DNA from each of these tissues were almost completely separated in two-dimensional plots of principal components (PC) scores. This indicates that significant and specific structural modifications in DNA occur in the progression of normal tissue to BPH and normal tissue to prostate cancer, and that the modifications are unique for each of the two progressions. The structural alterations are reflected primarily in spectral regions representing vibrations of the nucleic acids, phosphodiester and deoxyribose structures. The separation and classification of the normal prostate versus BPH or adenocarcinoma is shown using logistic regression models of infrared spectra. Similarly, logistic regression models of DNA spectra are used herein to evaluate the relationship between BPH and prostate cancer.

In the present characterization of DNA from prostate tissue, wavenumber-absorbance relationships of infrared spectra analyzed by principal components analysis (PCA) are expressed as points in space. Each point represents a highly discriminating measure of DNA structural modifications that altered vibrational and rotational motion of functional groups of DNA, thus changing the spatial orientation of the points. Application of PCA/FT-IR technology to prostate tissue provides a virtually perfect separation of clusters of points representing DNA from normal prostate tissue, BPH and adenocarcinoma (prostate cancer). The progression of normal prostate tissue to BPH and to prostate cancer appears i:o involve structural alterations in DNA that are distinctly different. Models based on logistic regression of infrared spectral data are used to calculate the probability of a tissue being BPH or adenocarcinoma. Remarkably, the models have a sensitivity and specificity of 100% for classifying normal versus cancer and normal versus BPH, and close to 100% for BPH versus cancer. Thus, the present invention shows that PCA/FT-IR technology is a powerful means for discriminating between normal prostate tissue, BPH and prostate cancer, with applicability for risk prediction and clinical application.

Although is it likely that the most popular use of the invention may be to assess the health of an individual organism with respect to cancer, it will be evident to those in a variety of arts that there are other uses. For example, the invention permits the analysis of environmental hazards. By analyzing DNA (as described herein) of an organism after exposure to an environment of unknown genotoxicity and comparing that profile to one obtained from DNA of the organism prior to its introduction to the environment (or comparing to an organism in a nonpolluted environment), an assessment of the genotoxicity of the environment can be made. In a preferred embodiment, the species of the organism in a nonpolluted environment is identical to that of the organism in the environment of unknown genotoxicity. As used herein, the term "nonpolluted environment" includes without any chemical contamination or the absence of a specific pollutant or pollutants.

The following examples are offered by way of illustration and not by way of limitation.

EXAMPLES

Examples 1

Prostate Cancer

A. Tissue Acquisition, DNA isolation and PCA/FT-IR Spectral Analysis: After excision, each tissue was flash frozen in liquid nitrogen. All tissues were kept at −80° C. prior to use and DNA was maintained under an atmosphere of pure nitrogen during the extraction procedure to avoid oxidation. DNA was isolated from the tissues and aliquoted for FT-IR spectroscopy (about 20 $\mu$g). Each DNA sample was completely dried by lyophilization, purged with pure nitrogen, and stored in an evacuated, sealed glass vial at −80° C. A total of 31 tissue samples were used. Five samples of prostate tissue obtained from individuals who died by accidents were examined histologically and found to be normal. These served as controls. Eighteen samples of benign prostatic hyperplasia (BPH) and eight samples of adenocarcinoma (cancer) served as test samples, each comprising a portion of the histologically identified lesion. All samples were obtained from the Cooperative Human Tissue Network, Cleveland, Ohio, together with related pathology data.

The IR spectra were obtained using the Perkin-Elmer System 2000 equipped with an I-series microscope (The Perkin-Elmer Corp., Norwalk, Conn.). For PCA/FT-IR spectral analysis, each spectrum was normalized across the range of 1750 to 700 cm$^{-1}$, as described above. This yeilded a relative absorbance value for each wavenumber, with a mean of 1.0. Euclidean distance was used to define the difference between a pair of spectra either for the entire spectrum or for a sub-region. This standard distance measure is defined as the square root of the sum of squared absorbance differences between spectra at each of the wavenumbers considered (e.g., 1051 for the entire spectral region 1750–700 cm$^{-1}$). The Euclidean distance can also be expressed in a more descriptive form as a percent. The numerator of the percent is the Euclidean distance divided by the square root of the number of wavenumbers for a region. The denominator used here for the percent for any region is the mean normalized absorbance between 1750–700 cm$^{-1}$, which is 1.0 for every case.

Principal components (PC) analysis (PCA) was used to identify a few variables (components) that capture most of the information in the original, long list of variables (the spectral absorbances at each wavenumber). This reduction in the number of variables is analogous to the process in educational testing whereby many individual test scores, such as in reading and arithmetic, are combined into a single academic performance score. Four PC scores (e.g., four dimensions) were found to be sufficient to describe the 1051 dimensions of the normalized spectra. PC scores were calculated with the grand mean of all spectra subtracted from each spectrum. The nonparametric Spearman correlation coefficient was used to assess the association of PC scores with patient ages and Gleason scores. The nonparametric analysis was used because some of the distributions are skewed or are not normal ("bell-shaped") which can lead to a bias in statistical significance when estimated from the Pearson correlation coefficient.

Two cases, which were outliers, were omitted from these analyses, leaving 29 cases. The omitted BPH sample and the omitted cancer sample had spectra very different from the included cases. Their Euclidean distances from the most similar spectra were 52% and 41%, respectively. All other spectra differed from their "nearest neighbor" spectrum by at most 21%, with a majority of spectra differing by less than 11%. The two outlier spectra show drastically reduced absorbarnce in the region around 1650 cm$^{-1}$, representing vibrations of the nucleic acids.

The Kruskal-Wallis and Mann-Whitney tests were used to determine if the three groups had similar diversity, defined as the mean distance of a spectrum to its group centroid. A permutation test was used to determine whether the three groups tended to cluster separately (representing an internal similarity of spectral properties in a group). The distance of each spectrum to its nearest neighbor in its own group (either normal, BPH, or cancer) was calculated, and the mean of these nearest neighbor distances for all of the spectra was the test statistic. The test was carried out by randomly permuting group membership labels 10$^3$ times and recalculating the test statistic each time. A smaller observed distance to the nearest neighbor than that obtained by random relabelling of groups is an indication of clustering. A nonparametric, rank-based version of this test was carried out by expressing each distance as a rank. For each spectrum, the distances to other spectra were ranked and the permutation test was carried out as described above, but with distances replaced by ranks. The test statistic was a mean rank. Again, a smaller observed mean rank than the mean obtained from random permutation is an indication of clustering. Both the test using distance and the test using ranks were carried out for the entire spectrum, 1750–700 cm$^{-1}$, and for several subregions.

Finally, logistic regression analysis was used as a model to determine if PC scores could be used to discriminate between pairs of DNA groups (normal versus BPH normal versus cancer and BPH versus cancer). The logistic regression analysis yields a risk score, which is a linear combination of PC scores, and a predicted probability of a sample being in one of the two groups considered (e.g, the probability of being BPH when BPH is compared to normal). These predicted probabilities, along with a chosen probability cut point, can be used to classify samples and provide estimates of sensitivity and specificity, or percent of samples correctly classified. For each analysis a cut point was chosen that jointly maximized sensitivity and specificity.

B. Clustering in PC Plots: PCA/FT-IR spectral analysis yielded four components (four PC scores per case) which explained a total of 90% of the spectral variation over 1051 wavenumbers. That is, most of the features of the 29 spectra could be described by four PC scores (labeled PC 1, PC2, PC3, PC4). The first two PC scores explained 76% of the variation and were adequate for two-dimensional representation (FIG. 1). FIG. 1 shows that the three groups were distinctly clustered. The two outliers omitted from the analysis are also represented on this plot and appear to the right of the main clusters.

The actual distance of the outlier points to other points is larger than that shown in this two-dimensional plot due to differences represented by other dimensions. The permutation test for clustering of groups (1750–700 cm$^{-1}$) yielded P=0.1, based on the distance measure, and P=0.01 using the nonparametric ranking technique (Table 1). The greater significance obtained by the ranking method arises from the relative isolation of one or two cases from the core of their group (FIG. 1), a configuration which influences the distance measure more than the ranking measure. Using these techniques, significant clustering was obtained for two regions of the spectrum: 1174–1000 cm$^{-1}$ (assigned to strong stretching vibrations of the PO$_2^-$ and C-O groups of the phosphodiester-deoxyribose structure) and 1499–1310 cm$^{-1}$ (assigned to weak NH vibrations and CH in-plane deformations of the nucleic acids). The P-values for mean distance and mean rank for these regions ranged from 0.02 to <0,001 (Table 1). The significance levels obtained strongly reject the null hypothesis that the observed clustering of the three groups occurred by chance. Overall, the findings indicate that DNA is altered in ways that produce clustering and, consequently, discrimination between normal prostate, BPH and prostate cancer DNA (FIG. 1; Tables 1 and 2).

Figures 1, 2A:
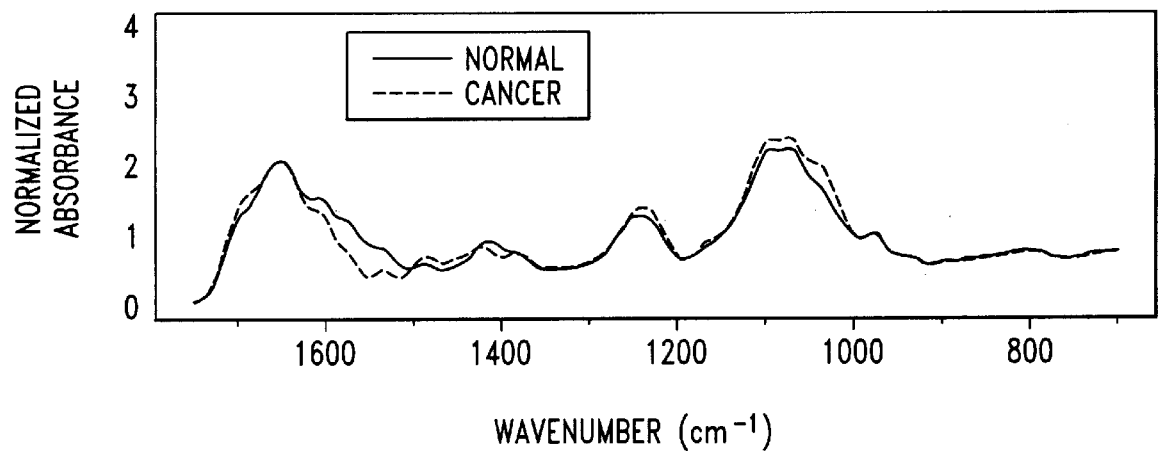
Figures 2, 2A:
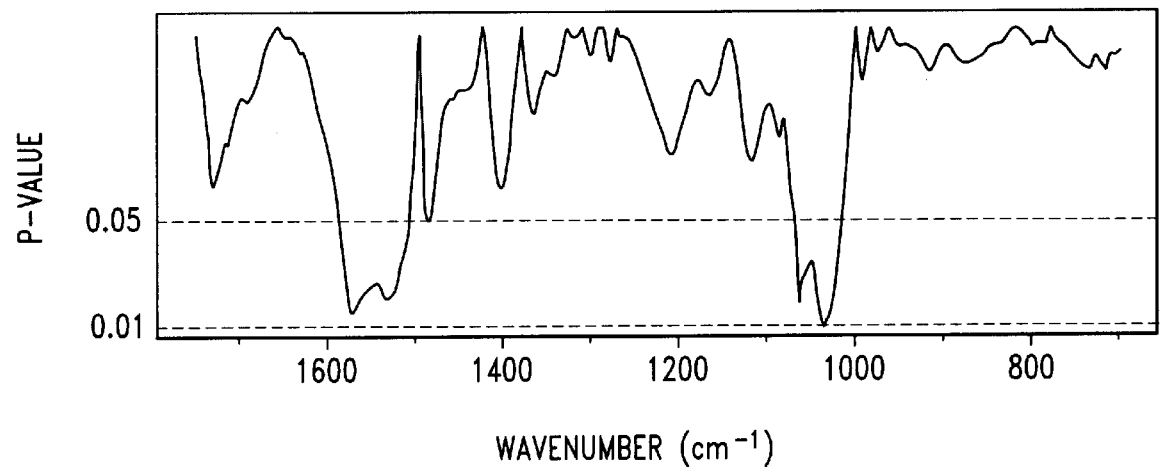
FIG. 2 shows a comparison of the mean spectrum of prostate cancer vs. normal tissue (FIG. 2A), BPH vs. normal tissue (FIG. 2B) and prostate cancer vs. BPH (FIG. 2C). The lower plot of each panel (A–C) shows the statistical significance of the difference in mean absorbance at each wavenumber, based on the unequal variance t-test. P-values are plotted on the $\log_{10}$ scale.
Figures 1, 2B:
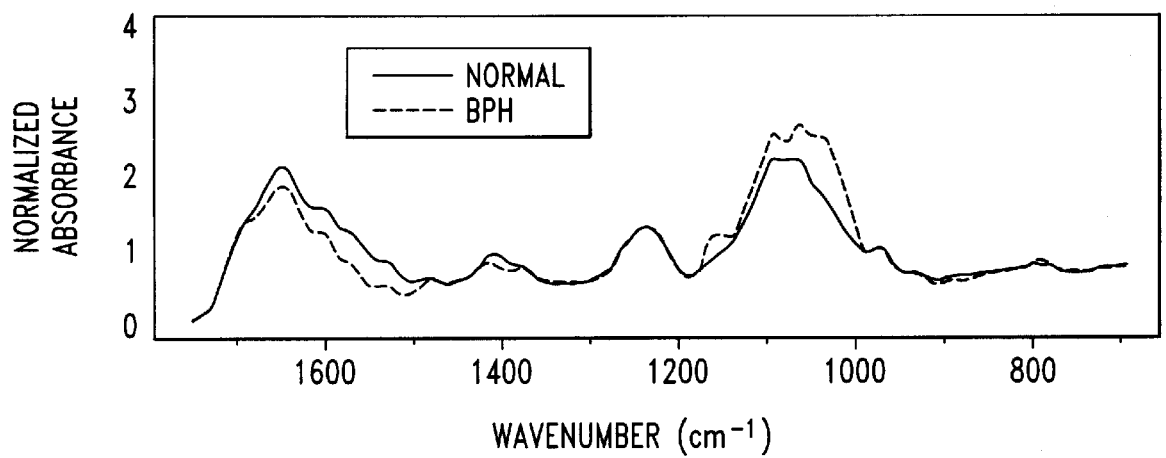
Figures 2, 2B:
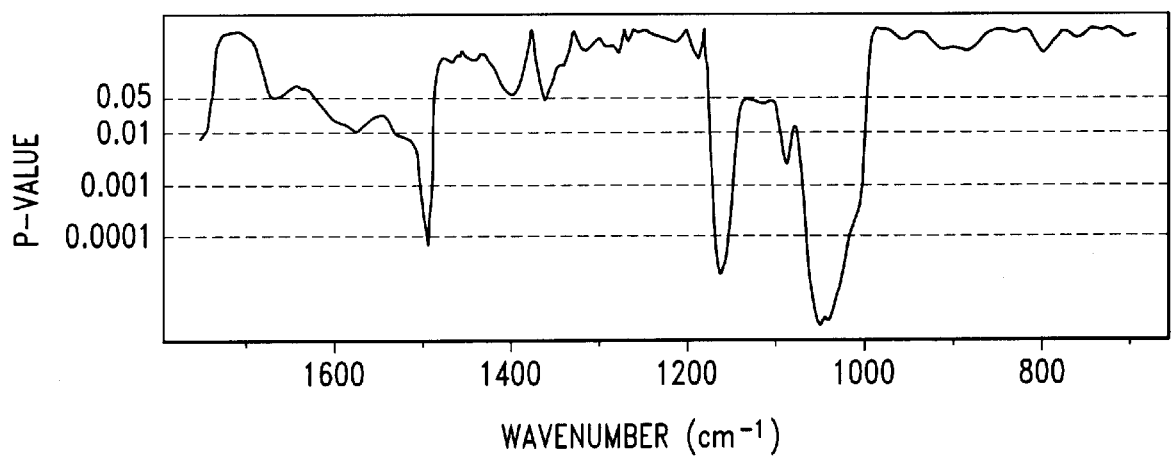
Figures 1, 2C:
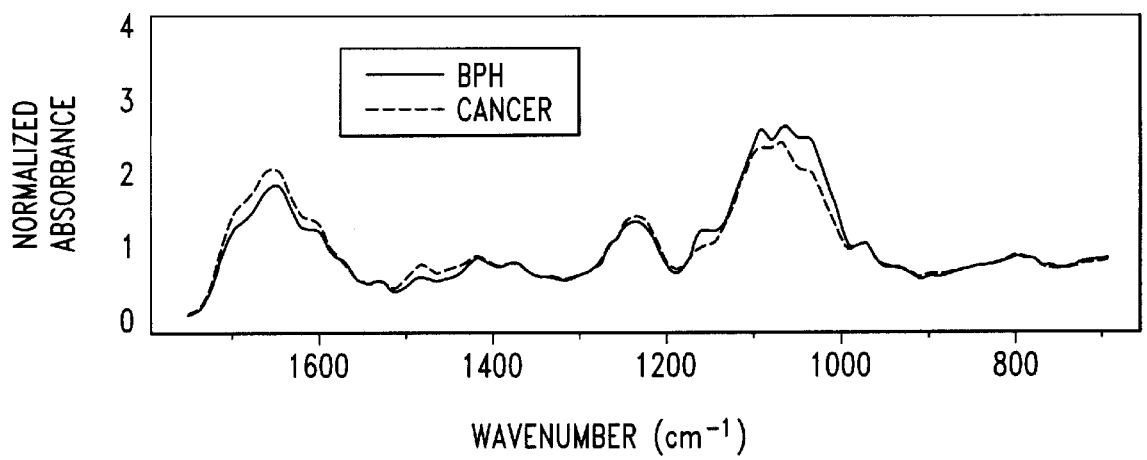
Figures 2, 2C:
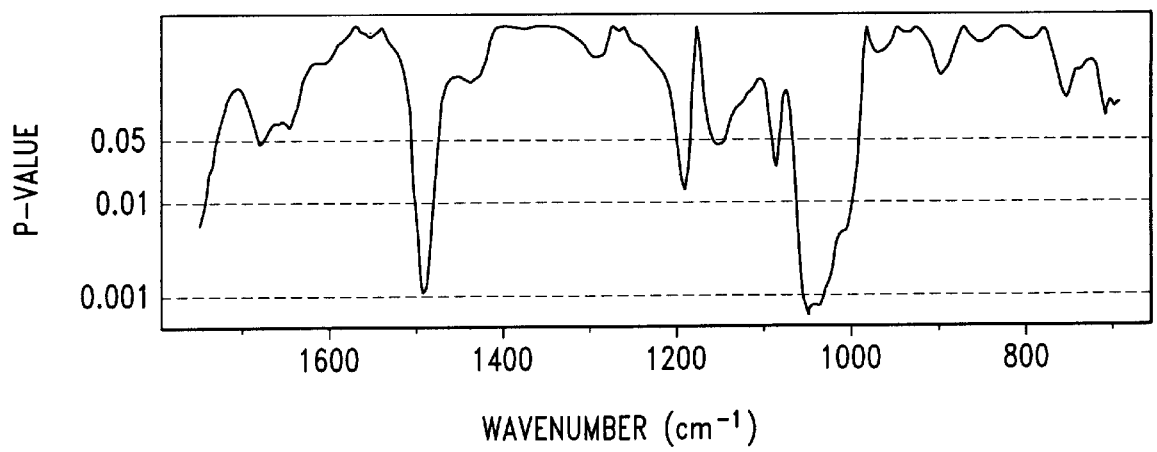

Detailed comparisons were made between the spectra of pairs of groups: normal vs. cancer, normal vs. BPH and BPH vs. cancer. The statistical significance of differences in mean normalized absorbance between groups was assessed for each wavenumber between 1750–700 cm$^{-1}$, using the unequal variance t-test (FIG. 2; A–C). The plot shows the comparison of the mean spectrum for each of the two groups, as well as the P-value from the t-test. The regions with P$\leq$0.05 represent differences between groups (e.g. normal vs. cancer) which are much less likely to be due to chance than regions with P>0.05. Each of the spectral comparisons between groups shows statistically significant differences in areas of the spectrum assigned to vibrations of the phosphodiester-deoxyribose structure and the nucleic acids. The spectral regions with significant differences in absorbance for the phosphodiester-deoxyribose structure are similar ($\approx$1050–1000 cm$^{-1}$); however, absorbances associated with the nucleic acids vary among the groups. That is, for the normal-cancer comparison, the region of significant difference is primarily $\approx$1475–1400 cm$^{-1}$ (C=O stretching and NH bending vibrations), whereas for the normal-BPH comparison it is $\approx$1600–1500 cm$^{-1}$. The comparison for BPH-cancer is focused at $\approx$1500 cm$^{-1}$. For the normal-BPH and BPH-cancer comparisons, significant differences are shown between $\approx$1175 to 1120 cm$^{-1}$, a region that likely includes symmetric stretching vibrations of the PO$_2$ group. The difference in means at all of these spectral regions is apparent from the plots of mean spectra per group in FIG. 2. The structural modifications are pivotal in the spatial distribution of points in the PC plot (FIG. 1) and in the pronounced discrimination between clusters (Table 1).

TABLE 1

Mean distance to nearest neighbor of same group and permutation test for non-random clustering. Distance is expressed as a percent difference between spectra; $10^3$ permutations were performed for each spectral sub-region.

| Spectral region ($cm^{-1}$) | ob-served | Mean distance[1] random per-mutation | P-value | ob-served | Mean rank[2] random per-mutation | P-Value |
|---|---|---|---|---|---|---|
| 1750–700  | 12.2 | 12.8 | 0.1  | 2.0 | 3.0 | 0.01   |
| 1750–1500 | 12.3 | 12.3 | 0.5  | 2.4 | 3.0 | 0.09   |
| 1499–1310 | 5.9  | 6.5  | 0.02 | 1.6 | 3.0 | <0.001 |
| 1309–1175 | 6.7  | 6.5  | 0.7  | 3.0 | 3.0 | 0.5    |
| 1174–1000 | 13.2 | 15.0 | 0.02 | 2.0 | 3.0 | 0.01   |
| 999–700   | 6.9  | 7.4  | 0.1  | 2.3 | 3.0 | 0.05   |

[1]Mean Euclidean distance to nearest neighbor in the same group expressed as a percent.
[2]Mean rank of Euclidean distance of each spectrum to nearest neighbor in the same group.

C. Cluster diversity: The diversity of the three groups, expressed as the mean distance to the group centroid, did not differ significantly (p=0.8). However, the normal prostate group was slightly less diverse (mean distance=11.7%) than was the BPH group (mean distance=14.5%) or prostate cancer group (mean distance=13.9%). Increased structural diversity generated in primary tumors is likely an important factor in selecting DNA forms that potentially give rise to malignant cell populations.

Figure 3A:
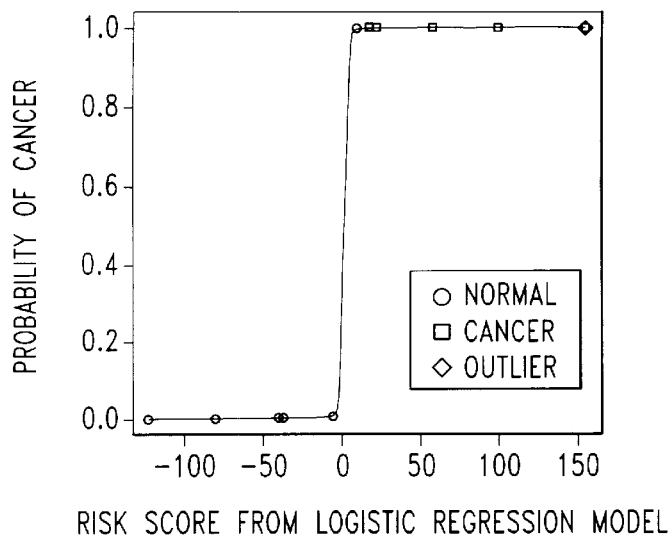
FIG. 3 shows Sigmoid curves depicting the probability of DNA being classified as normal tissue versus prostate cancer (FIG. 3A), normal tissue versus BPH (FIG. 3B), and BPH versus prostate cancer (FIG. 3C). The curves are based on the logistic regression models depicted in Table 2 below. The predicted probabilities rise very rapidly over a narrow range, which reflects a high degree of discrimination among groups and a precipitous change in DNA structure associated with the normal to BPH and normal to prostate cancer progressions. Each sample is plotted at its predicted probability.
Figure 3B:
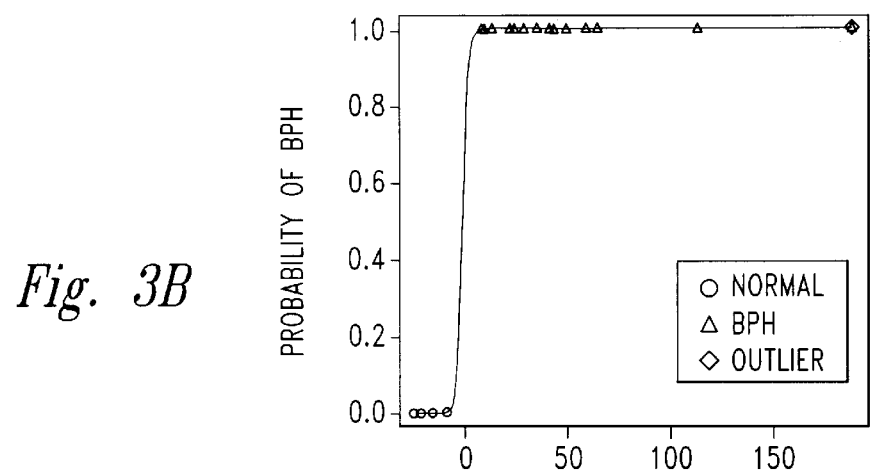
Figure 3C:
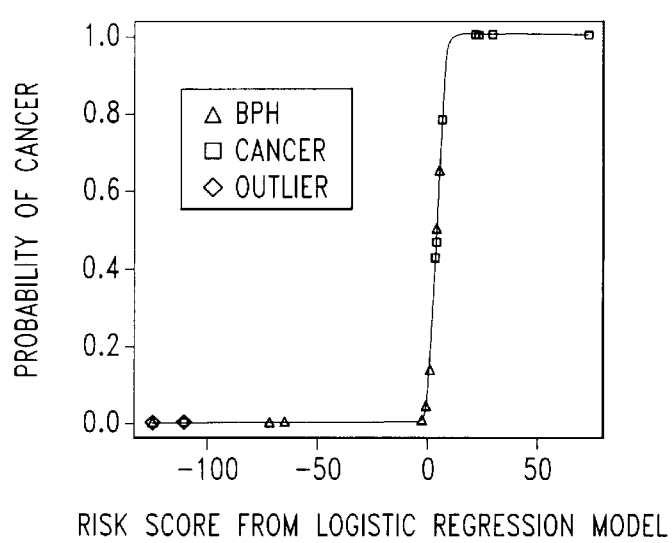

D. Group Classification: PC scores can be readily used to classify patients into groups when pairs of groups are compared using logistic regression. The logistic regression model (Table 2) is an equation which yields a risk score, R, when the values of the PC scores are inserted into the equation. R is transformed to a probability by the following standard statistical equation: probability=exp(R)/[1+exp(R)]. A cut point is chosen and if the probability exceeds this cut point, the case would be classified as BPH. The actual cut points are noted below. As shown in Table 2, the model for normal versus cancer and normal versus BPH correctly classifies each group 100% and 100% overall (P-values in each case were <0.001). The correct classification rate for cancer versus BPH was close to 90%, based on a designation of "cancer" for a predicted probability of $\geq 0.1$. (Probability cut-points of 0.15 to 0.41 achieve the same correct classification rates in the BPH vs. cancer comparison.) The predicted probabilities based on the models in Table 2 are given in FIG. 3. The individual risk score is based on the appropriate PC model (Table 2) and the predicted probability is a mathematical function of the risk score. as noted above. All of the BPH and cancer cases have predicted probabilities extremely close to 1.0 and all of the normal cases have predicted probabilities of $\leq 0.002$ when BPH or cancer are compared to normal cases. These marked distinctions in predicted probabilities confirm the clear separation of groups, as shown in FIG. 1. When cancer is compared to BPH, predicted cancer probabilities ranged from 0.42 to 1.00 and predicted BPH probabilities ranged from 0.00 to 0.65.

The two outliers omitted from the analyses tend to support the findings. The outlier BPH and cancer points lie to the right in the PC plot (FIG. 1). This is the same direction found with the progressions from normal to BPH and from normal to cancer, suggesting that the outlier DNAs have a higher degree of structural modification. When the models shown in Table 2 were used to classify the two outliers, the BPH outlier was correctly classified, using the normal versus BPH model, with a predicted BPH probability close to 1.0. The cancer outlier is also correctly classified in the normal versus cancer model with a predicted cancer probability close to 1.0. In the BPH versus cancer model, the BPH outlier is correctly classified with a predicted cancer probability close to zero: however, the cancer outlier is incorrectly classified as a BPH with a cancer probability close to zero.

TABLE 2

Logistic regression models for probability of BPH (vs. Normal), Cancer (vs. Normal) and Cancer (vs. BPH). Normal, n = 5. BPH, n = 17. P-values are based on the null hypothesis that each model is not predictive of group membership. P-values are calculated from a chi-square test on change in deviance.

| | | Coefficients ± Standard Errors | | | | Correct Classification Rate | | | |
|---|---|---|---|---|---|---|---|---|---|
| Model | Intercept | PC1 | PC2 | PC3 | PC4 | By Group | | Overall | P-Value* |
| normal vs. BPH    | 24.9 ± 0.1  | 5.2 ± 0.2  | 5.8 ± 0.04 | 3.9 ± 0.03 | —           | normal: 100%; | BPH: 100%    | 100% | <0.001 |
| normal vs. Cancer | 34.3 ± 0.1  | 12.0 ± 0.04 | —         | —          | −21.0 ± 0.1 | normal: 100%; | Cancer: 100% | 100% | <0.001 |
| BPH vs. Cancer    | −14.5 ± 8.1 | −4.5 ± 2.6 | —          | —          | −11.1 ± 6.3 | BPH: 88%;     | Cancer: 100% | 92%  | <0.001 |

*P-value for the null hypothesis that the probability of a case falling into a specified group is unrelated to the PC scores.

E. Age and Gleason Score relationships: Age does not appear to be a factor in creating the pronounced distinctions among groups, although the incidence of prostate cancer increases significantly over the age of 50 years. The age ranges for the three groups were 16–73 years for normal (n=5); BPH, 58–73 (n=17); and cancer, 61–76 (n=7). Among the Spearman correlations of age with each of the four PC scores, none were statistically significant (P<0.05). In all, 28 correlations were considered, consisting of age correlated with each PC score in each of the three groups, as well as in all pairs of groups (e.g.. age correlated with each PC score in normal and BPH tissue combined) and in the entire pooled set of 29 cases. Spearman correlations ranged in magnitude from 0.01 to 0.59 with P=0.09 to P=1.0. The most significant correlation was r=−0.51 between age and PC4 in the combined normal and cancer groups (P=0.09). When PC4 was omitted from the logistic regression analysis and models were based on PC1–PC3, the P-values corresponding to those in Table 2 were, top to bottom, P<0.001, P<0.001 and P=0.005, again supporting a non-random distinction among the groups. These results based on PC4 and the weak or nonsignificant correlations between age and other PC scores do not support any role for age in the ability to use spectra to distinguish among the groups.

The Gleason score, which uses microscopically evinced architectural changes to classify tumor status, had little association with the PC scores, although based on the n=7 cancer cases, there was limited power to detect other than strong associations. Spearman Correlations of PC scores 1–4 with the Gleason score ranged from −0.49 to +0.26, with P=0.2 to 0.8.

F. Logistic Regression Models of Probability: The Sigmoid curves (FIG. 3) for the prostate show sharp transitions between the normal and cancer states and normal and BPH states. These transitions are characterized by a lack of cases at intermediate probabilities, corresponding to the clear separation of groups in FIG. 1. Thus, at some point in the modification of DNA, critical structural changes apparently take place that lead to a rapid increase in cancer probability.

BPH is not known to be etiologically related to prostate cancer, however, it is of interest that the BPH versus prostate cancer curve (FIG. 3C) shows several cases having intermediate probabilities. The configuration of cases in FIG. 1 also provides some insight into the controversial view that BPH is a direct precursor of prostate cancer. The findings do not support this concept in that the BPH group lies "beyond" the cancer group, starting from the normal group. This positioning suggests that a transition from BPH to cancer would involve a reversal of some of the spectral transitions shown to be associated with cancer, or that there are additional changes in the BPH DNA that mimic a reversal in the progression to cancer. Alternatively, modifications may result in DNA structures that lead to a variety of nonneoplastic lesions, including, BPH. Although BPH may not be a direct precursor of prostate cancer. PCA/FT-IR spectral analysis may provide a promising means of predicting the occurrence of prostate cancer, based on the structural status of BPH DNA.

The absence of transition states in the normal to cancer and normal to BPH curves is of interest. This is likely due to the fact that "transition" tissues having DNA values between zero and 100% probability (FIG. 3, A–C) were not part of this study.

Evidence with the prostate suggests that DNA structure is progressively altered in response to factors in the microenvironment, notably the •OH, that are likely etiologically related to the development of cellular lesions, prostate tumors (adenocarcinoma) and BPH. Intervention to forestall or correct the genetic instability of these tissues and likely increase in cancer risk should focus on controlling the cellular redox status and •OH concentrations. The approaches may include control of the iron-catalyzed conversion of $H_2O_2$ to the •OH (Imlay et al., *Science* 240: 640–642, 1988); regulation of •OH production resulting from redox cycling of hormones (Han and Liehr, *Carcinogenesis* 16: 2571–2574, 1995) and environmental xenobiotics (Bagchi et al., *Toxicology* 104: 129–140, 1995); and antioxidant/reductant therapy (Ames et al., *Proc. Natl. Acad. Sci. USA* 90: 7915–7922, 1993; Bast et al., *Am. J. Med.* 91(Suppl. 3C):2S–13S, 1991).

Example 2

Breast Cancer

A. Tissue Acquisition, DNA Isolation and PCA/FT-IR Spectral Analysis: Tissues were obtained from local Seattle hospitals and The Cooperative Human Tissue Network (Cleveland, Ohio). A total of 12 tissues were obtained from 12 patients with invasive ductal carcinoma of the breast but having no lymph node involvement (IDC), of which one was multifocal (the second focus being a signet ring cell carcinoma which was not evaluated) and one was bilateral breast cancer (only one of which was evaluated). A total of 25 tissues were obtained from 25 patients with invasive ductal carcinoma having one or more lymph nodes positive for metastatic cancer ($IDC_m$). No unusual histologies occurred among the non-metastatic and metastatic groups with the exception of the two IDCs mentioned. Tumor size was based on the maximum dimension of the tumor, as recorded in the pathology reports. Non-cancerous breast tissue (RMT) was obtained from 21 patients who had undergone hypermastia surgery (reduction mammoplasty). Routine pathology showed no cellular changes other than occasional non-neoplastic (e.g., fibrocystic) lesions in these tissues.

After excision, each tissue was flash frozen in liquid nitrogen and stored at −80° C. DNA was isolated from the tissues, dissolved in deionized water, and aliquoted for FT-IR spectroscopy (~20 μg). Each DNA sample was completely dried by lyophilization, purged with pure nitrogen and stored in an evacuated, sealed glass vial at −80° C. All samples were analyzed by FT-IR spectroscopy.

The IR spectra were obtained using The Perkin-Elmer System 2000 equipped with an 1-series microscope (The Perkin-Elmer Corp., Norwalk, Conn.). Each spectrum was specified by the absorbance at each integer wavenumber from 2000 to 700 $cm^{-1}$. Only the interval from 1750 to 700 $cm^{-1}$, which included all major variations among spectra, was included in this analysis. A baseline adjustment and normalization was carried out. One RMT was represented by two sections. The mean of the two adjusted and normalized spectra was used in these analyses. The multiplicative normalizing factor was applied to absorbencies between 1750 and 700 $cm^{-1}$. Using deuterium exchange, no evidence was found to suggest that absorbed moisture contributed to the spectral properties of DNA.

B. Statistical Analysis: For analysis of overall DNA structure employing FT-IR analysis. Principal Components Analysis (PCA) was used. PCA methodology is a statistical procedure applied to a single set of variables with the aim of discovering a few variables (components) that are independent of each other and which capture most of the information in the original, long list of variables. The methodology can greatly reduce the number of variables of concern. The PCs partition the total variance by finding the first PC (a linear combination of the variables) which accounts for the maximum amount of variance for the entire population. The PCA methodology then finds a second combination, independent of the first PC, such that it accounts for the next largest amount of variance. This procedure continues until a number of independent PCAs are found that explain a significant portion of the total variance. In the present context, PCA was a way to identify major features of absorbance-wavenumber variation across a collection of spectra and describe that variation succinctly.

Using PCA, it is possible to identify a few components that serve as "building blocks" for the spectra. After the PCA, each spectrum can be represented by a few PC scores. PCA was carried out with the grand mean spectrum subtracted from individual spectra. Prior to the analysis, it was decided to retain enough components to explain at least 90% of the total variation (around the mean) of the data set. To determine if some of the differences among spectra might be due to age, the correlation between age and each PC score was calculated. To visualize the spectral relationship of the cancer and non-cancer groups ($IDC_m$, IDC and RMT), plots were constructed based on their first three PC scores. These two and three dimensional plots permit the simultaneous examination of two or three of the most significant components of any single specimen data set and permit the meaningful comparison of each data set to one another.

Figure 4:
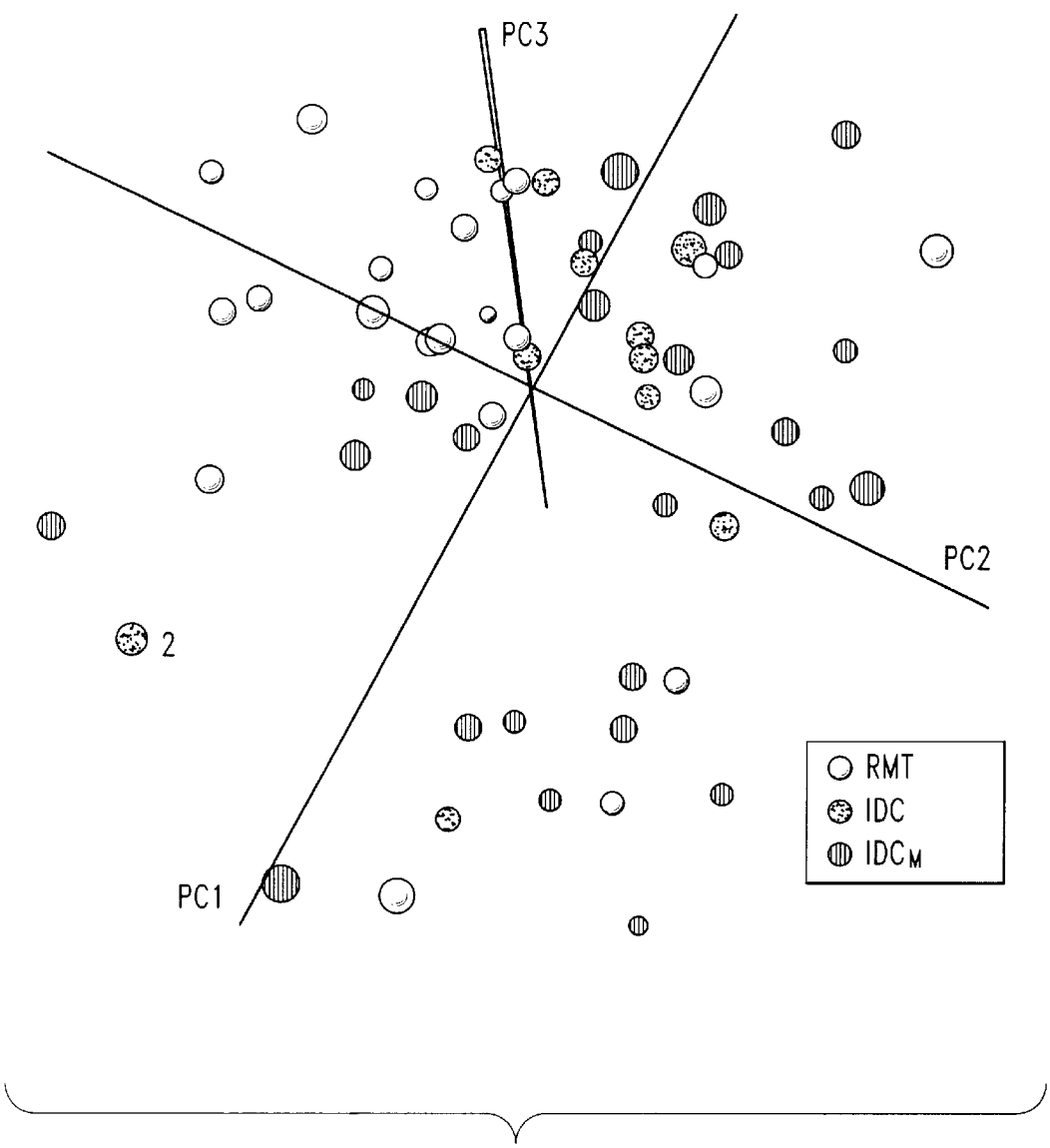
FIG. 4 is a three-dimensional plot of PC 1, 2 and 3 wherein each sphere represents a DNA absorbance spectrum and the location of a sphere is determined by the "shape" of the spectrum, including height, width and location of absorbance peaks. The core cluster of non-invasive ductal carcinoma of the breast ("IDC") spheres in the upper part of the plot (medium stipple) is significantly smaller than the more diverse and larger $IDC_m$ cluster (heavy stipple), and the reduction mammoplasty tissue ("RMT") and metastatic invasive ductal carcinoma ("$IDC_m$") clusters substantially overlap and are not statistically different in size.

C. Principal Components Analysis of Spectral Profiles: Spectral profiles revealed great diversity of the $IDC_m$ group and homogeneity of the IDC group. FIG. 4 shows a three-dimensional representation of the spectra based on PCA. The position in this plot is determined by the absorbance spectrum, mainly expressed as the height, width and location of peaks. There is a core cluster of IDCs in the upper part of the plot (indicated by yellow spheres). The two IDCs in the lower left part of the plot are outliers well removed from the core cluster. Notably, these are: 1) an IDC with a second focus of signet ring cell carcinoma and 2) a bilateral breast cancer. As apparent from the plot, both the $IDC_m$ cluster (magenta) and the RMT cluster (blue) are considerably larger-indicating, greater spectral diversity-than the core IDC cluster.

The size of a cluster can be measured and its spectral diversity represented by the mean distance of the members from the centroid of the cluster. This distance can be expressed as an approximate percent difference in normalized absorbance per wavenumber between a cluster member and the mean spectrum for the cluster, which lies at its centroid. The distance expressed as a percent difference is calculated as: a) 100% times the square root of the mean squared difference in normalized absorbance across wavenumbers 1750 to 700 $cm^{-1}$, which is then b) divided by 1.0 the approximate mean normalized absorbance for most spectra. For the comparison of cluster sizes, three RMTs, three $IDC_m$s and two IDCs that lay at outlier distances from the centroid in each group were removed to define a core cluster for the RMT, $IDC_m$, and IDC. All outliers had at least a 20% difference from any member of their cluster. Based on centroids and distances of the remaining cases, the spectral diversity (mean distance from the centroid) was 12.4% for the $IDC_m$ group, 7.3% for the IDC group, and 9.2% for the RMT group. An approximate P-value for the difference in diversity between groups was based on the Mann-Whitney test, comparing distances to the centroids without outliers: P=0.003 for IDC vs. $IDC_m$, P=0.04 for RMT vs. $IDC_m$ and P=0.4 for RMT vs. IDC. (The P-values are approximate because dependence among distances is introduced through the calculation of the common centroid.)

Based on initial PCA of the 58 samples (RMT, N=21; IDCm, N=25, IDC, N=12), four outliers were detected-specimens whose FT-IR spectra departed strikingly from the rest of the group and which had outlier PC scores. The PCA was repeated initially eliminating these four outliers. The PC scores were then calculated for these outliers in a manner similar to the others (subtracting the grand mean spectrum of the 54 samples and then projecting each of the residua, spectra on the PC eigenvectors). It was found that 91% of the variation in absorbance of the 54 samples was explained by the first five components. This implies that variation among spectra is highly structured. The 1051 wavenumbers from 1750 to 700 $cm^{-1}$ constitute potentially 1051 dimensions of variation. Over 90% of this variation can be represented by only 5 dimensions.

There were only weak correlations of PC scores with age, but some correlations were statistically significant for all samples combined. Correlations between age and PC scores were as follows: r=0.21 for component and age (P=0.1), r=0.29 for component 2 (P=0.003), r=0.03 for component 3 (P=0.8), r=0.25 for component 4 (P=0.06) and r=0.30 for component 5 (P=0.02). The small magnitude of these correlations suggests very little influence of age on spectral structure. Further, even the statistically significant correlations (PC-2 and PC-5) appear to be an artifact because correlations between the PC scores and age in the cancer and non-cancer groups separately are very weak-less the 0.18 in magnitude-and are non-significant (minimum P=0.4). There is a broad range of ages for all groups which should allow a substantial true correlation to be detected: 17 to 89 for all samples. 26 to 89 for cancer ($IDC_m$ and IDC) and 17 to 63 for RMT. There was also no statistically significant correlation of the PC scores with the number or percent of positive lymph nodes.

Figure 5A:
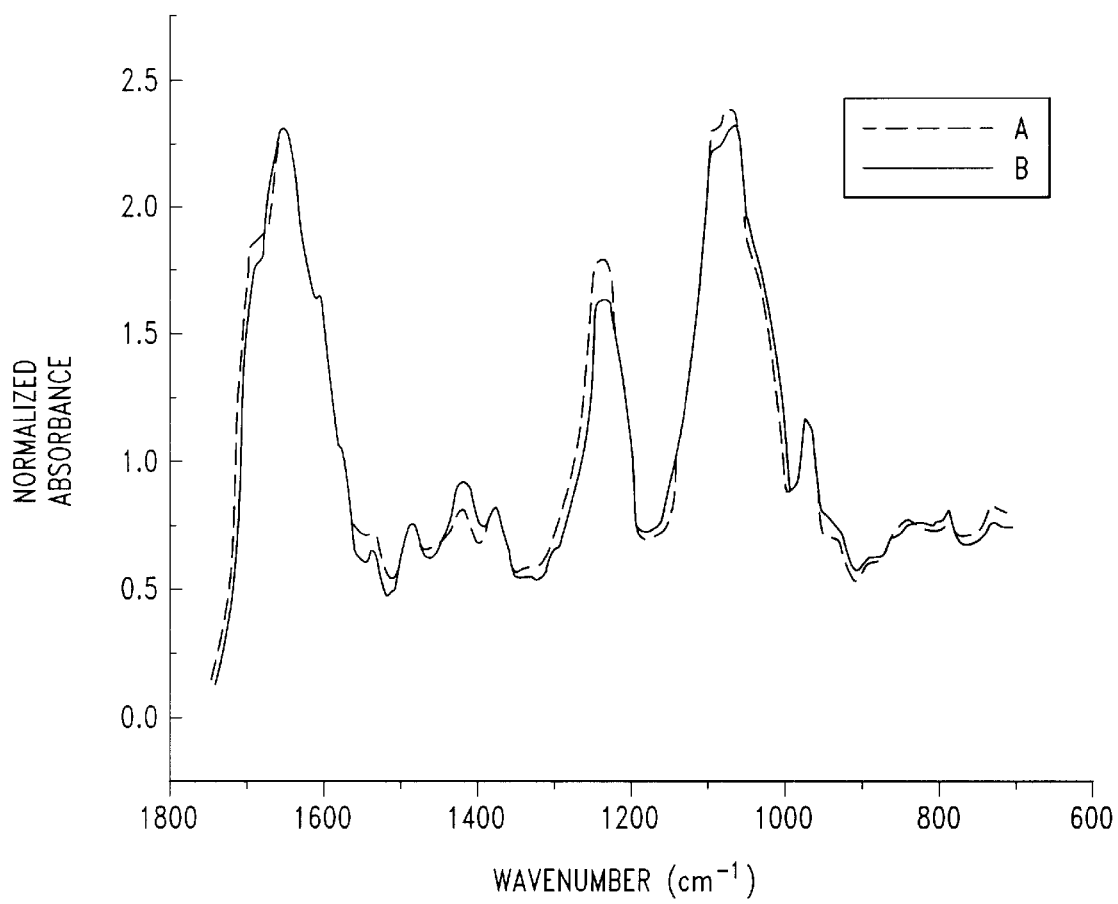
FIG. 5A shows two spatially close IDC spectra (see arrows indicating A and B on the three-dimensional PCA plot) wherein the two overlaid spectra shown in FIG. 5B differ by a mean of only 3% in normalized absorbance, demonstrating the high specificity of the PCA and the fact that spatially close spheres have almost identical spectral profiles.
Figure 5B:
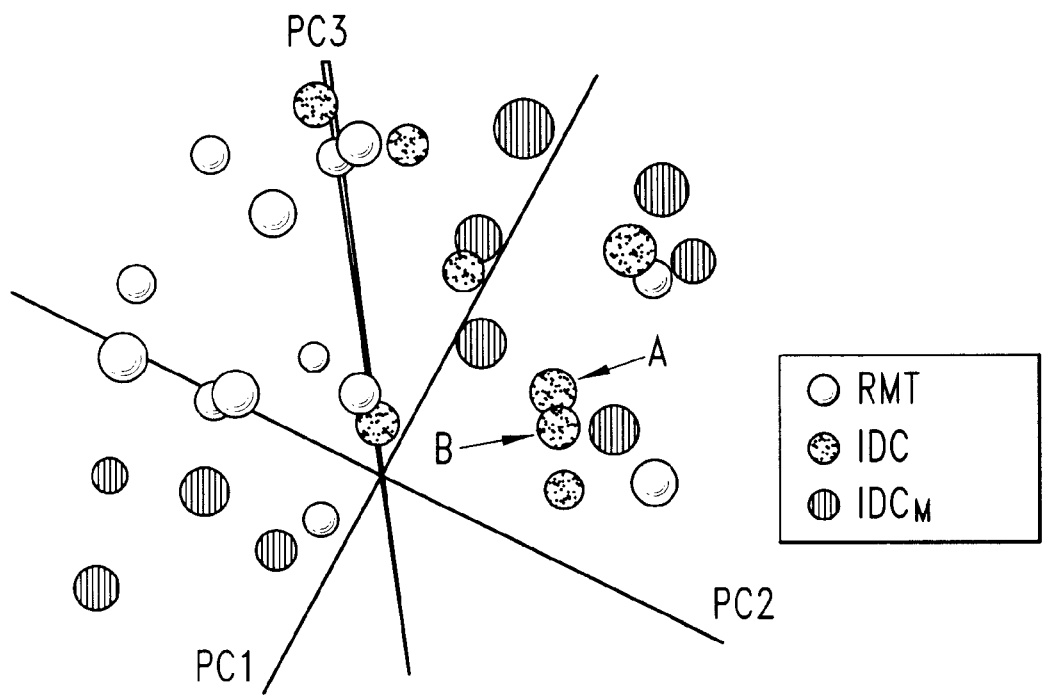
Figure 6A:
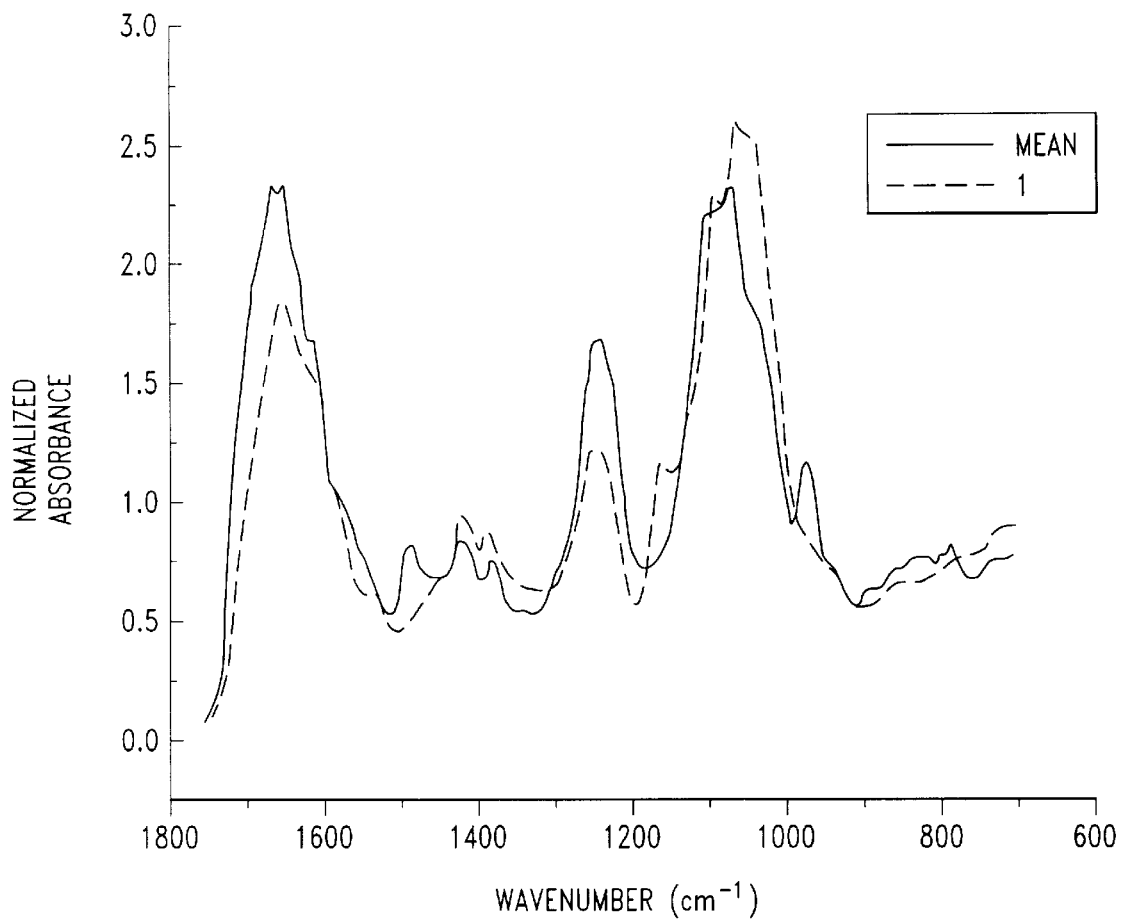
FIG. 6A and 6B show the spectral profiles of two IDC outliers (identified in FIG. 5) compared to the spectral profile of the mean IDC core cluster; "1" represents a multifocal carcinoma, with one focus being a highly malignant signet ring cell carcinoma, and "2" represents a bilateral breast cancer. In each case, the dramatic difference between the mean and outlier spectrum is apparent over most of the spectral region (see text for wavenumber—structural relationships) illustrating the pronounced structural specificity associated with the PCs analysis.
Figure 6B:
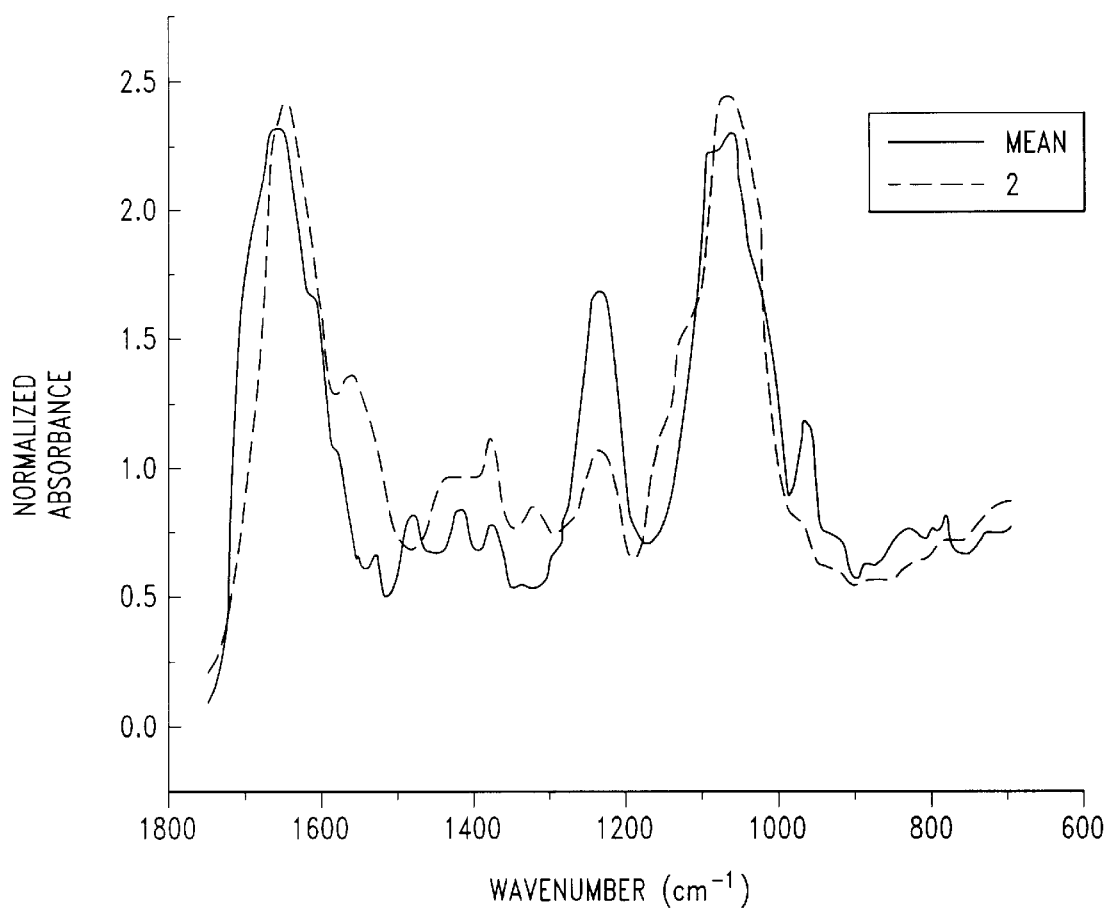

FIG. 5A depicts the overlaid spectra of the two "outliers" ("A" and "B" in FIG. 4) that lie close together on the three-dimensional PCA plot shown in FIG. 5B. The actual spectra differ by only a mean of 3% in normalized absorbance, indicating high precision in characterizing spectral phenotypes. The two IDC outliers mentioned earlier are also distinct in spectral profile from the core IDC cluster. FIGS. 6A and 6B show these two spectra superimposed on the mean normalized spectrum of the IDC core cluster. Differences are notable over most of the spectral area, but especially in the following regions: 1700 to 1350 $cm^{-1}$, the peak at about 1240 $cm^{-1}$, and about 1180 to 900 $cm^{-1}$. These regions generally represent N—H and C—O vibrations of the bases. $PO_2$ anti-symmetric stretching vibrations of phosphodiester groups, and C—O vibrations of deoxyribose, respectively.

Figure 7:
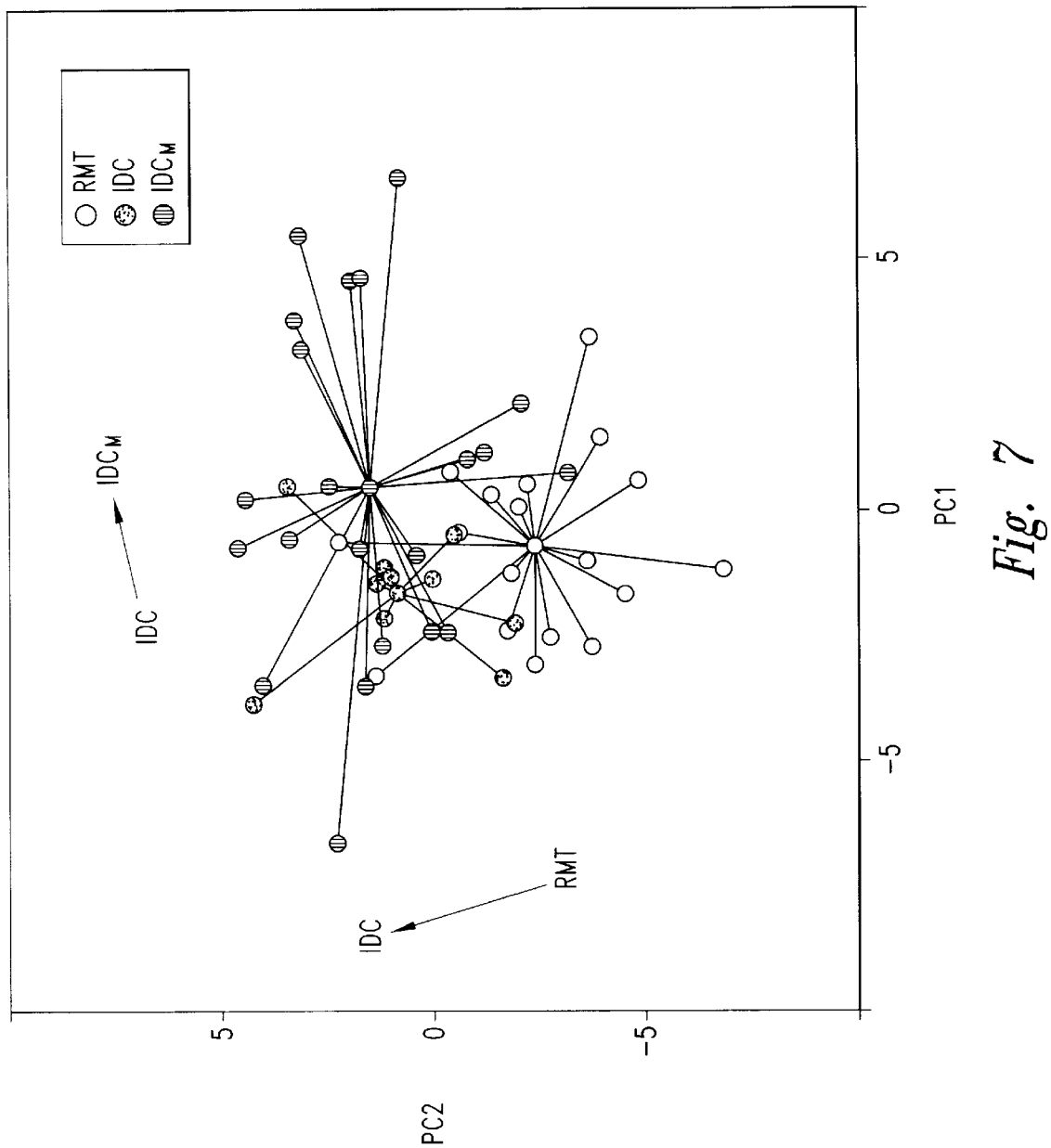
FIG. 7 shows a centroid calculation of the spectra for the RMT, IDC, and $IDC_m$ specimens on a graph plotting PC2 vs. PC1, and the direction vectors from the RMT centroid to the IDC centroid, and the IDC centroid to the $IDC_m$ centroid.

It was described above that the centroid for a related data set (e.g., IDC specimens) could be calculated wherein the centroid would be considered the weighted mean for the spectra associated with a particular species of specimen. Such an activity is shown in FIG. 7 for PC1 and PC2 values for the three types of specimens subject to analysis. In this figure, the vector from the centroid for RMT specimens to the centroid for the IDC specimens is shown on the left hand side of the graph and represents the shift of spectral profiles from a RMT to an IDC state. This direction constitutes an initial direction and establishes a reference for comparison to the vector derived from the IDC centroid to the $IDC_m$ centroid. The degree of vector rotation, relative to the RMT-IDC vector, is shown in Table 3.

TABLE 3

| Spectral Region | Change in Direction | 95% Confidence Interval for Change | P Value |
| --- | --- | --- | --- |
| 1750–700 ($cm^{-1}$) | 94° | 66–129° | <0.001 |
| 1750–1550 ($cm^{-1}$) | 86° | 52–127° | <0.001 |
| 1549–1300 ($cm^{-1}$) | 127° | 93–154° | <0.001 |
| 1299–1200 ($cm^{-1}$) | 113° | 77–164° | <0.001 |
| 1199–850 ($cm^{-1}$) | 108° | 65–146° | <0.001 |
| 849–700 ($cm^{-1}$) | 83° | 28–148° | <0.001 |

It therefore can be seen that the effect on DNA from the IDC state to the $IDC_m$ state is not only widespread over the analyzed spectrum, but relatively consistent. Moreover, the implication of this directional change lends support to the proposition that as attacks continue on DNA, there is a definite, quantifiable, and predictable movement of the DNA spectral profile from one state to another.

Figure 8:
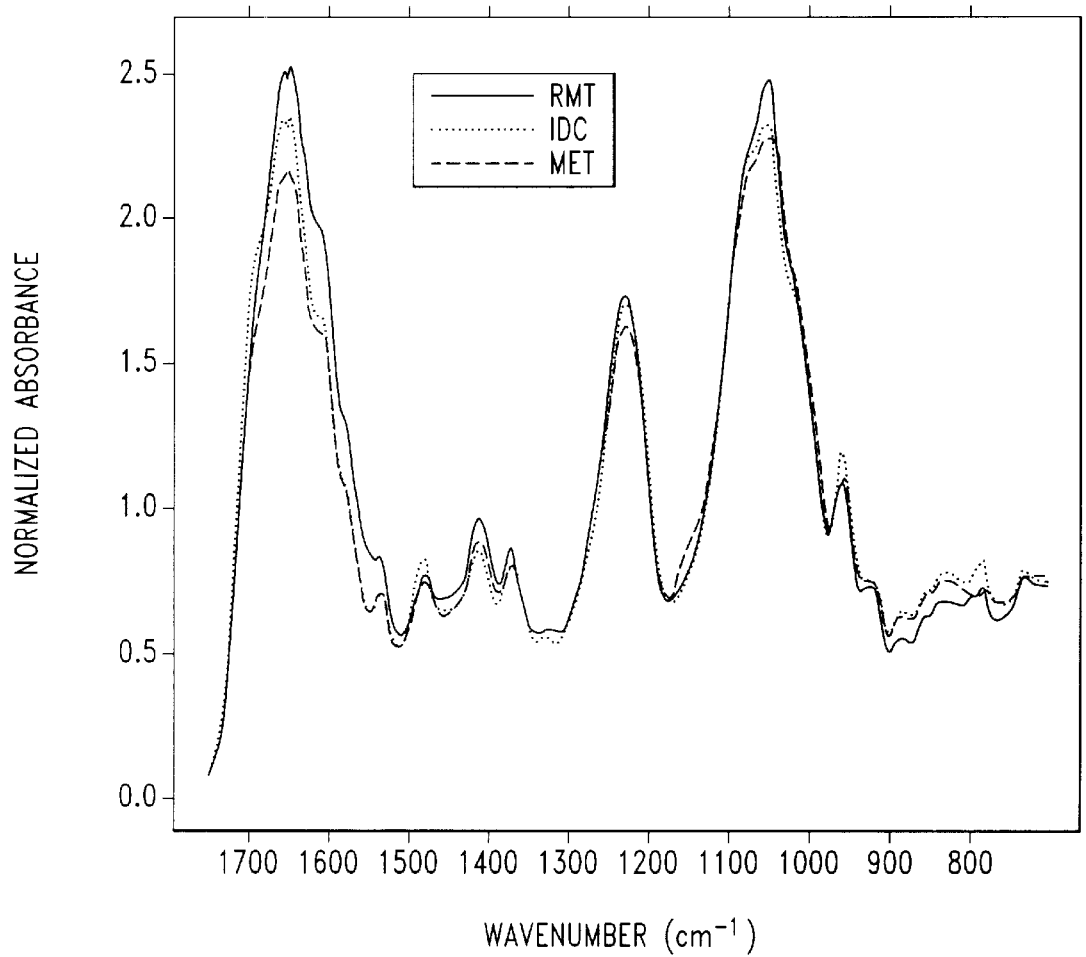
FIG. 8 shows a centroid spectra overlay for the average RMT, IDC, and $IDC_m$ species.
Figure 9:
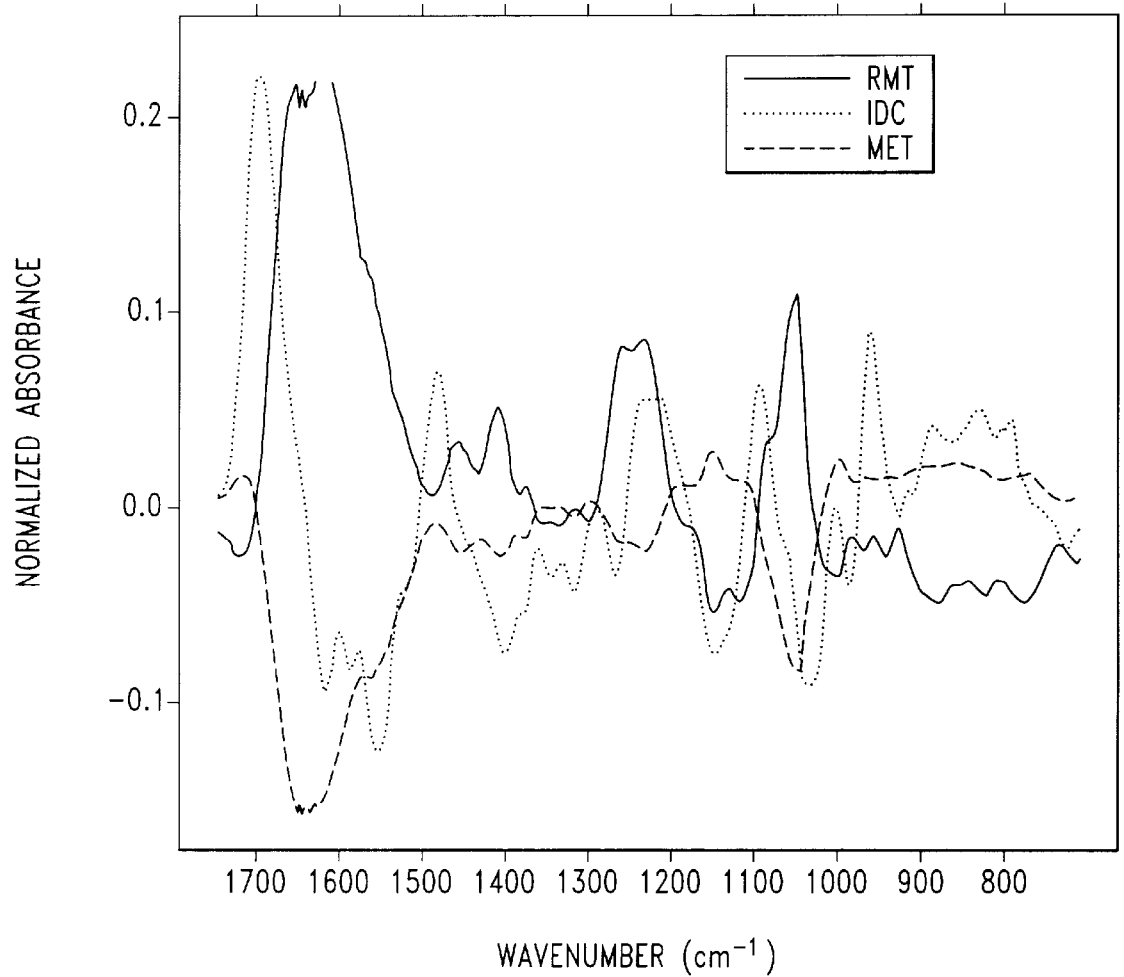
FIG. 9 shows a centroid spectra overlay for the average RMT, IDC, and $IDC_m$ species after subtracting the mean, thus emphasizing the spectral differences between the species.

FIGS. 8 and 9 are presented to emphasize the spectral distinctiveness between the three species of specimens. In FIG. 8, the spectra for each centroid for each species is shown. After having subtracted out the grand mean from these curves, the mean deviations for each species make readily discernible the distinguishing spectra inherent between the species as is best shown in FIG. 9.

Figure 10:
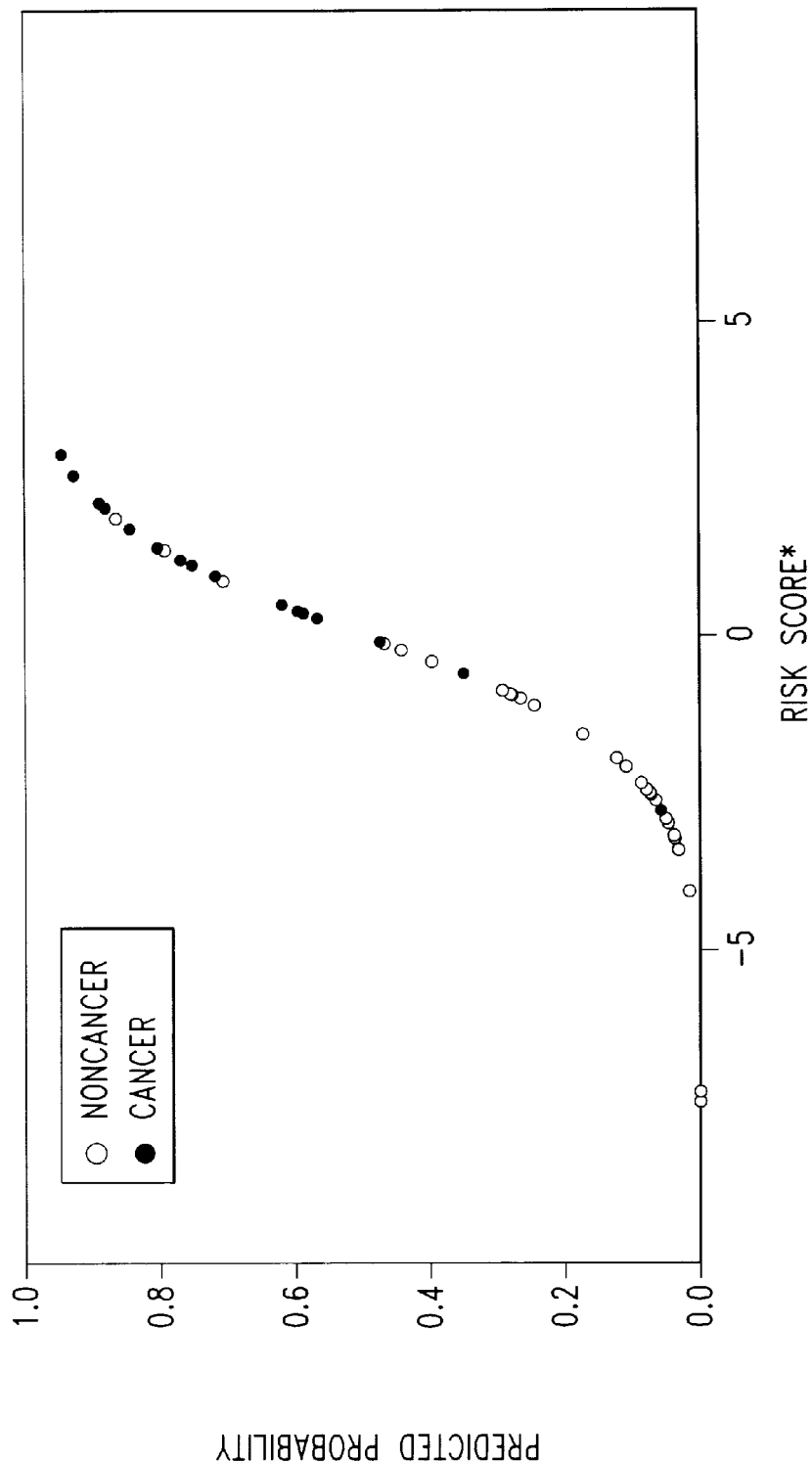
FIG. 10 shows the predicted probabilities of cancer based on FT-IR methodology.

In FIG. 10, a generally sigmoid curve is established using data sets generated by FT-IR. The transition from non-cancer to cancer is sharp, indicating that the manifestation of cancer can ultimately be initiated by a relatively small incentive, depending upon the "location" of the sample on the curve.

D. Alternative Means for Tissue Acquisition and Long-Term Storage: As an alternative means to the above described method for obtaining and preserving specimens for FT-IR analysis, it may be desirable to embed the specimen in a paraffin block after acquisition and initial preparation. When analysis of the specimen is desired, the paraffin-embedded tissue (PET) is dewaxed and the DNA is isolated by using conventional techniques such as application of phenol and/or chloroform solutions. After determining the purity of the specimen, the DNA is placed in an aqueous solution, dried under vacuum, and applied to the barium fluoride window for analysis by FT-IR.

The use of PET specimens for spectral analysis greatly increases the number of samples available for DNA analysis since it is not be necessary to wait and obtain special biopsies for analysis (specimens could be easily stored and retrieved at a later time), and permits retrospective follow-up studies of the same tissue specimens to be conducted rapidly and economically.

Example 3

Liver Cancer

A. Material and Methods: English sole were obtained from a relatively clean rural environment [Quartermaster Harbor, Wash.] and a chemically contaminated urban environment [Duwamish River, Seattle, Wash.]. Their livers were examined histologically and found to be cancer-free, although they contained various non-neoplastic lesions characteristic of fish from contaminated environments.

The Duwamish River flows into Puget Sound through a heavily industrialized area. The sediments contain a variety of carcinogens and other xenobiotics, such as polynuclear aromatic hydrocarbons and chlorinated pesticide residues; however, a restoration program is in progress to reduce the sediment contamination.

Two groups of sole were obtained from the Duwamish River (DUW93, n=8; and DUW95. n=10). Because of the restoration program, the DUW95 samples were expected to reflect significantly less sediment contamination than the DUW93 samples, but greater than the QMH samples. Fish from Quartermaster Harbor. Wash., served as controls (QMH, n=7). The lengths ± SD of the QMH, DUW95 and DUW93 fish were 29.5±4.2 cm, 23.6±1.6 cm and 24.1±0.8 cm, respectively. The weights were 254.3±115.0 g, 125.6±16.2 g and 125.0±22.5 g.

Isolation of DNA from hepatic tissue and PCA analyses of FT-IR spectra were undertaken as described above. Each FT-IR spectrum was normalized over the range 1750 to 700 $cm^{-1}$. PCA was used to identify a few variables (components) that capture most of the information in the original, long list of variables (the spectral absorbancies at each of the 1051 wavenumbers form 1750 to 700$cm^{-1}$). PC scores were calculated with the grand mean of all spectra subtracted from each spectrum. Thus, the PC scores represent variations in spectral (structural) features as they differ from the grand mean spectrum. The Kruskal-Wallis (KW) test and the Mann-Whitney (MW) test were used to calculate the statistical significance of difference,, in PC scores between groups. The same procedures were used to test for differences in spectral diversity, which was defined for a group as the mean distance of spectra to the group centroid. The unequal variance t-test was used to compare the mean normalized absorbance between groups. The t-test was carried out at each of the 1051 wavenumbers from 1750 –700 $cm^{-1}$. Fish age, reflected in length and mass, was a potentially confounding variable and this possibility was addressed in the analysis.

Figure 11:
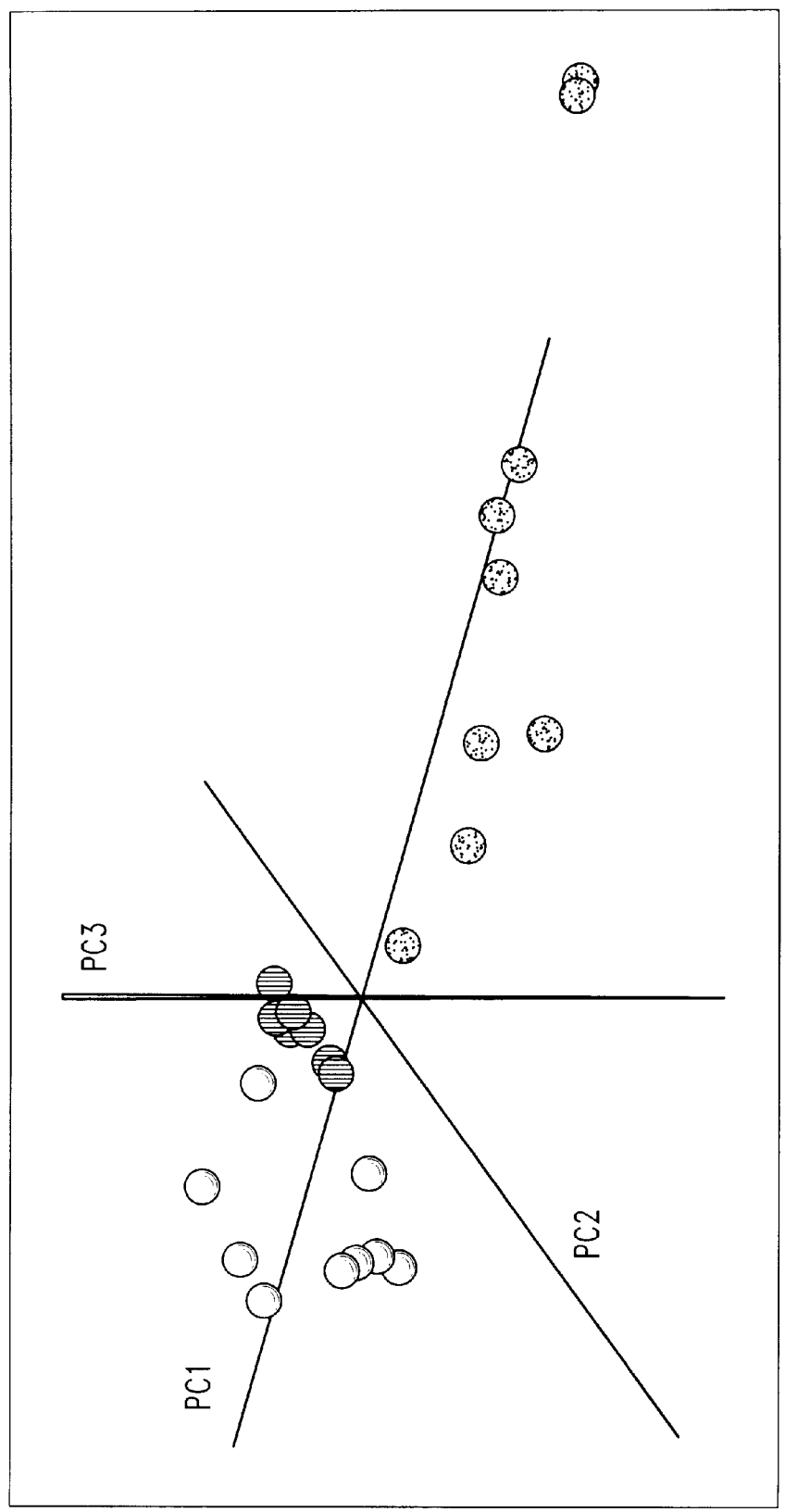
FIG. 11 shows a three-dimensional projection of the clusters of points derived from the first three PC scores, which summarize spectral features of the DNA from English sole inhabiting an essentially clean control environment (QMH group) or inhabiting a chemically contaminated urban environment (DUW group).
Figures 1, 12A:
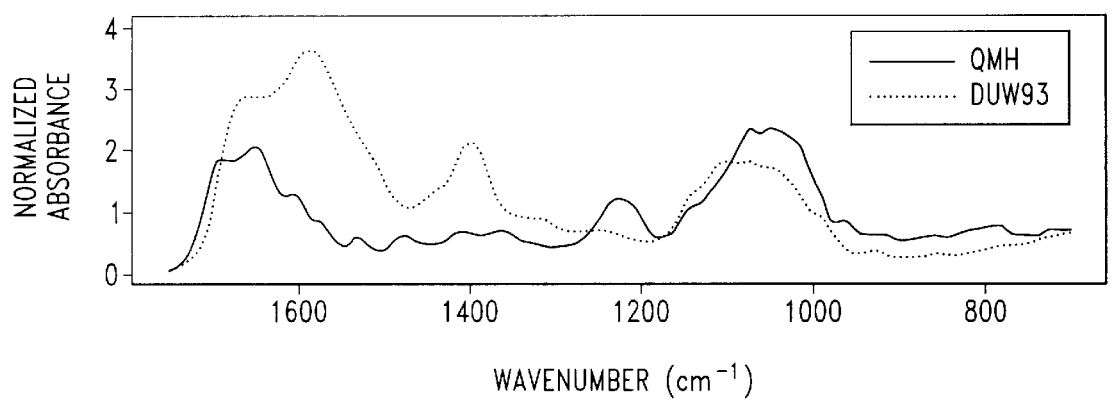
FIGS. 12A–12C show a comparison of the mean spectrum for each of a QMH group and a DUW group. The lower plot of each panel shows the statistical significance of the difference in mean absorbance at each wavenumber, based on the unequal variance t-test. P-values are plotted on the $\log_{10}$ scale.
Figures 2, 12A:
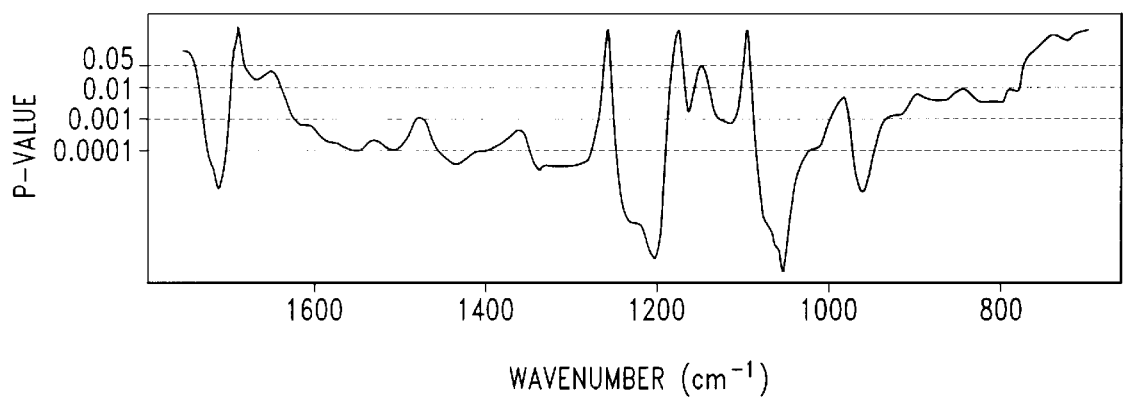
Figures 1, 12B:
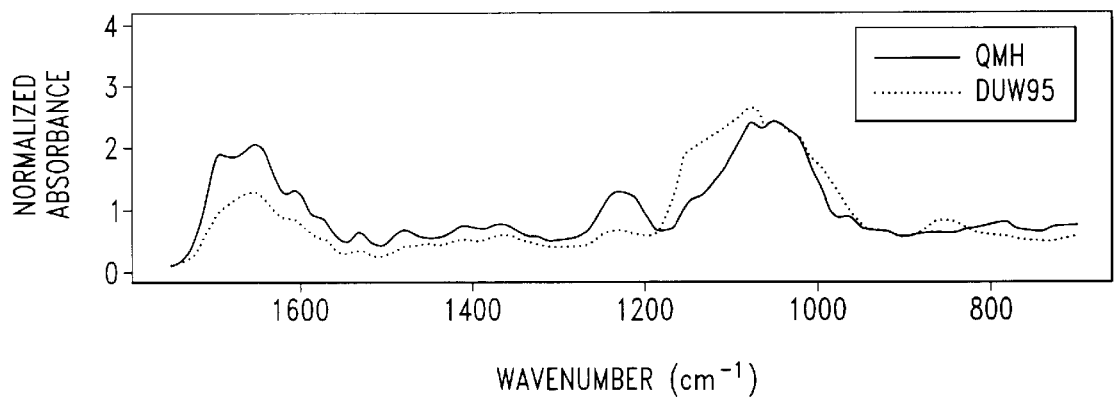
Figures 2, 12B:
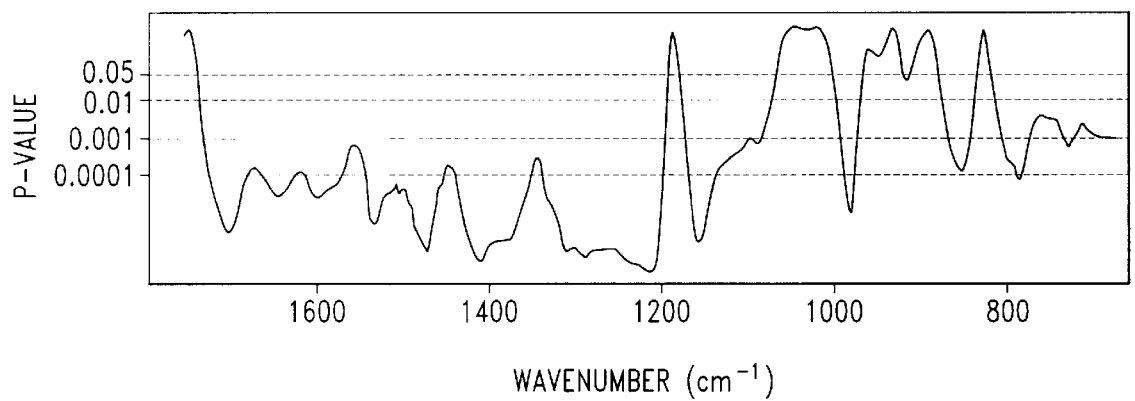
Figures 1, 12C:
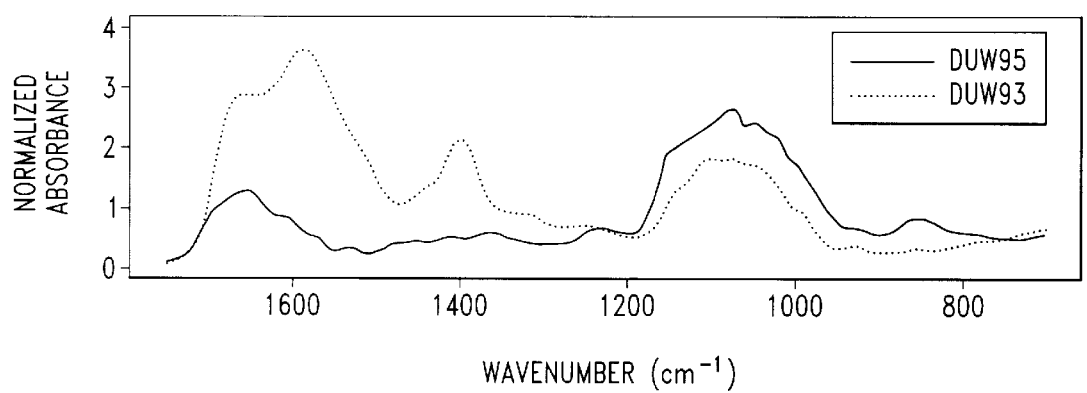
Figures 2, 12C:
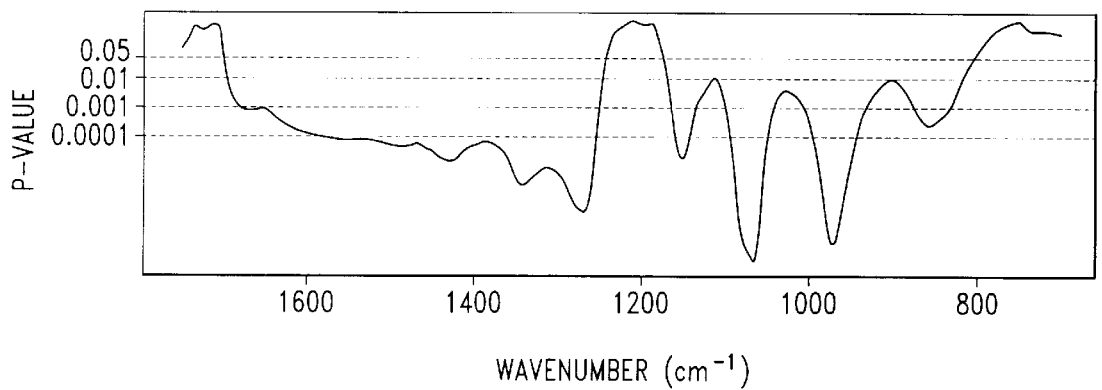

B. Results: FIG. 11 shows a PCA for the first three PC scores using specimens obtained from a location known not to be polluted (blue spheres); specimens obtained from an area known to be polluted (yellow spheres); and specimens obtained from the same polluted area prior to significant clean-up and/or environmental actions to remove polluted sediment (maroon spheres). As can be seen through inspection of the figure, a distribution similar to that encountered with breast tissue is present in the DNA of fish liver.

The clusters of points derived from the first three PC scores, which summarize spectral features of the DNA from the QMH and DUW groups, are shown in a three-dimensional projection (FIG. 11). The hypothesis that all groups have the same mean values of PC scores (thus, similar spectra) is rejected (KW P-value <0.001) and the hypothesis that any two of the groups have the same mean values of PC scores is also rejected (MW P-value 0.04 to <0.001). The three groups are distinct without any overlap (FIG. 11). PC1 and PC2, combined, account for 94% of the spectral variation and thus provide a good means for representing the variety of spectra encountered. PC3 is used for display purposes (FIG. 11), although it explains only 3% of the spectral variation.

The differences between groups occur at many frequencies. The upper part of each panel in FIG. 12 shows the mean spectrum for each of two groups (QMH –DUW93; QMH–DUW95, and DUW95–DUW93). The bottom part of the panel shows P-values for each spectral comparison, one P-value per wavenumber. The comparisons yield P<0.05 at 78–87% of the 1051 wavenumbers, thus demonstrating that the structures of the DNAs from the DUW93 and DUW95 groups are markedly different from each other and the QMH group. Accordingly, the findings substantially invalidate the null hypothesis that the mean, normalized spectra are equal between groups. The spectral differences are notable with respect to the antisymmetric stretching vibrations of the $PO_2$ structure ($\approx$1240 $cm^{-1}$). The band at this spectral region is present in the QMH group, but is virtually lost in the spectra of the DUW93 and DUW95 groups. Other major differences are evident in spectral regions representing vibrations associated with the nucleic acids ($\approx$1700 to 1450 $cm^{-1}$) and deoxyribose ($\approx$1150 to 950 $cm^{-1}$).

It is obvious (FIG. 11) that the samples can be 100% correctly classified into groups (separated) on the basis of the PC scores (Table 4).

TABLE 4

Principal component scores by group and statistical significance of differences between groups

| Variables | QMH<br>n = 7<br>Mean ± SD | DUW95<br>n = 10<br>Mean ± SD | DUW93<br>n = 8<br>Mean ± SD | KW<br>P-value<br>for overall<br>differences | MW<br>P-value<br>for QMH<br>vs.<br>DUW93 | MW<br>P-value<br>for QMH<br>vs.<br>DUW95 | MW<br>P-value<br>for DUW93<br>vs.<br>DUW95 |
|---|---|---|---|---|---|---|---|
| Principal component | | | | | | | |
| PC1 | −6.1 ± 14 | −12.8 ± 2.8 | 21.3 ± 12.3 | <0.001 | <0.001 | <0.001 | <0.001 |
| PC2 | 6.1 ± 1.3 | −3.3 ± 2.6 | −1.3 ± 1.4 | <0.001 | <0.001 | <0.001 | 0.04 |

Figure 13A:
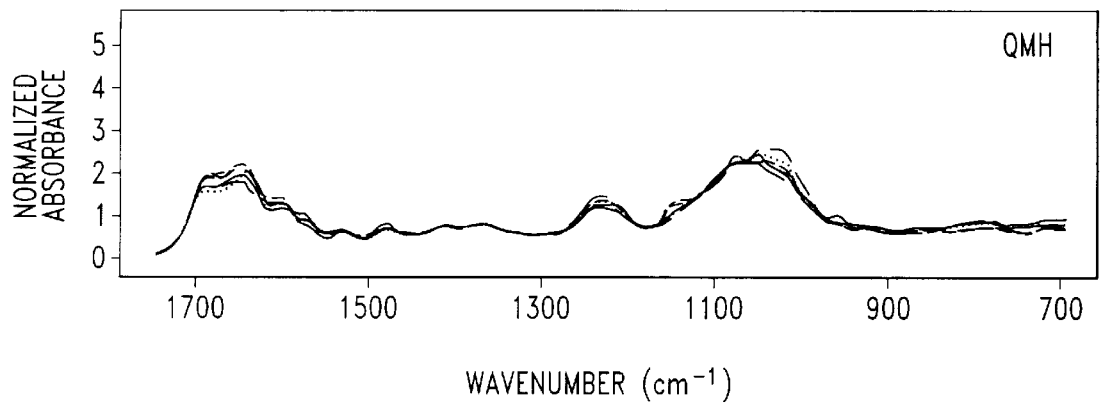
FIGS. 13 shows overlays of the individual spectra of QMH and DUW groups.
Figure 13B:
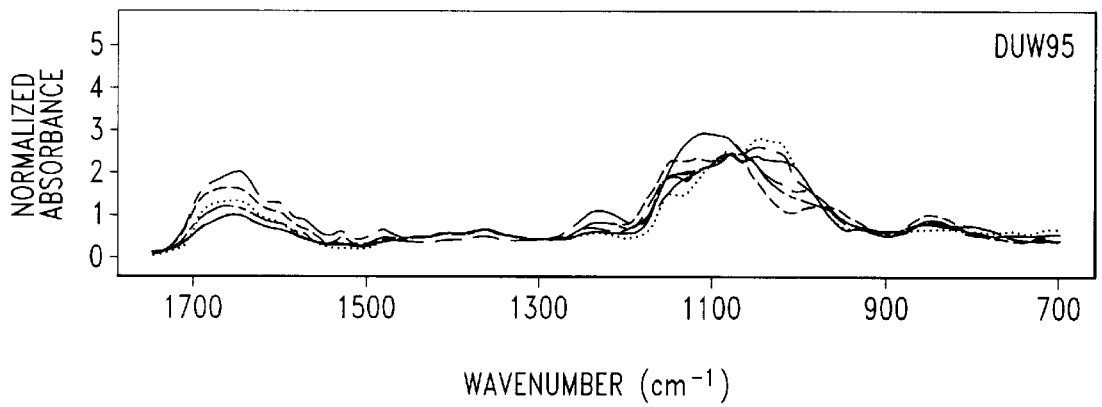
Figure 13C:
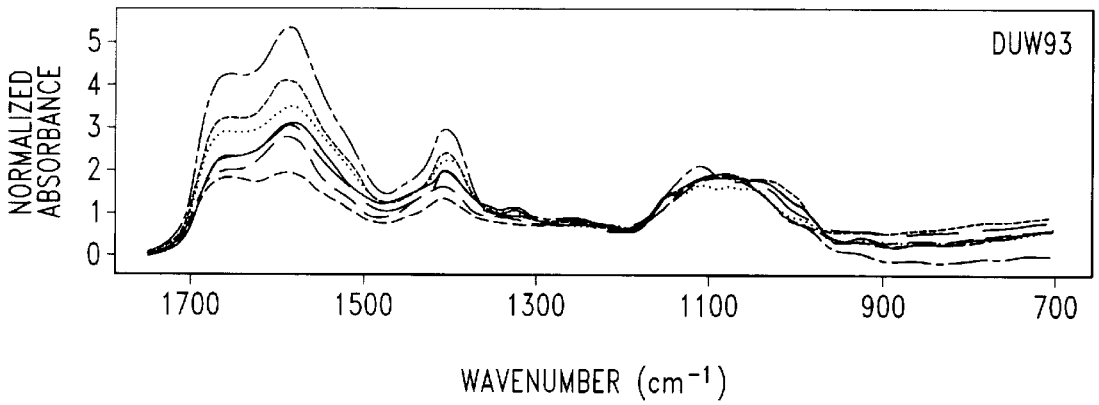

FIG. 11 shows that the diversity of spectra (note the spread of points) is substantially greater in the DUW93 and DUW95 groups, compared to the QMH group. The varying diversity between the groups and the spectral differences which separate them are also evident in FIG. 13 in which the individual spectra or each group are overlaid. The tightness of the QMH spectra and the increasing spectral diversity from the QMH to the Duwamish River groups is notable in the region ≈1700 to 1450 $cm^{-1}$, which includes strong C—O stretching and $NH_2$ bending vibrations of the nucleic acids. Also in the DUW93 group, compared to the other groups, there is a pronounced increase in absorbance and spectral diversity in the 1400 $cm^{-1}$ region assigned to weak NH vibrations and CH in-plane deformations of the nucleic acids. The region ≈1150 to 950 $cm^{-1}$, which includes strong stretching vibrations associated with deoxyribose, increases in spectral diversity from QMH to DUW95, but tightens in the DUW93 group. The differences between the spectral properties are consistent with the discrimination between groups shown in Table 4 and the increased diversity of the clusters illustrated in FIG. 11.

A formal test for diversity differences (KW test for the null hypothesis that all groups have the same mean distance to the group centroid) yields P=0.002, strongly suggesting unequal diversity among groups. These mean distances to the centroid provide a scale for measuring diversity. A larger mean distance indicates that a group is more spread out (FIG. 11), that is, the spectra are more diverse. The DUW95 group has a mean distance which is four times that of the QMH group, representing a four-fold greater diversity (Table 5). Two of the three pairwise comparisons of diversity are significant (p<0.05); however, the comparison between the DUW95 and DUW93 groups is not significant (MW P-value=0.2), although the DUW93 group (representing DNA with the most altered base structure) is more diverse than the DUW95 group.

TABLE 5

Spectral diversity for three groups

| Group | Distance to group centroid<br>(diversity)<br>Mean ± SD | N |
|---|---|---|
| QMH | 2.5 ± 1.0 | 7 |
| DUW95 | 5.8 ± 2.0 | 10 |
| DUW93 | 10.2 ± 7.2 | 8 |

P-values for null hypotheses: (1) all three groups have the same mean diversity, KW P-value = 0.002; (2) Mean QMH = Mean DUW95, MW P-value = 0.003; (3) mean QMH = mean DUW95, MW P-value = 0.2

The varying diversities of the groups is unlikely due to age variables. The QMH group is the most diverse in length and mass, yet it shows the least spectral diversity. The QMH group shows a length SD that is two to five times larger than that of the DUW95 and DUW93 groups and a mass SD that is five to seven times larger. However, the mean distance of the QMH spectra to their centroid is two to four-fold smaller than that of the Duwamish groups. These results would be highly inconsistent if age were a significant factor in spectral diversity. Length and mass also appear to have little effect in creating the spectral differences by location (FIG. 11). In regression analysis, length and mass combined explained only 7% of the variation in PC1 and 40% of the variation in PC2. PC1 is by far the more important component in explaining spectral diversity. Length and mass explain only about 9% of the overall spectral variation, whereas location explains 77%.

The DNA structures isolated from the QMH, DUW95 and DUW93 fish were each unique in that the PC plot revealed a complete separation of clusters (FIG. 11). In addition, the DNAs from the exposed groups were substantially more diverse than those of the control group and the DUW93 group was more diverse than the DUW95 group (Table 5, FIG. 11). These distinctions which were not significantly age-related, likely arose from structural features induced in DNA by different environmental factors. Among the environmental factors likely contributing to the cluster separations and the differences in diversity are the type, degree and duration of exposure to toxic chemicals in the sediments. Striking differences occurred between the three groups in regions of the spectra assigned to the nucleic acids and the phosphodiester-deoxyribose structure (FIGS. 12 and 13), suggesting that alterations in these structures contributed substantially to the separation of clusters and the differences in diversity among groups.

There was a statistically significant increase in the diversity of clusters representing the two Duwamish River groups, compared to the tight cluster of the reference group (FIG. 11; Table 5). Increased diversity may be especially important in carcinogenesis in that it sets the stage for the selection of DNA forms that give rise to malignant cellular phenotypes. The high degree of diversity in the exposed fish groups may serve the same function.

Cluster separation in PC plots was described above in studies of prostate (Example 1) and breast (Example 2) cancer. With the prostate, for example, perfect discrimination was achieved between DNA from normal and adenomacarcinoma tissue. Similarly, perfect discrimination was obtained between clusters in this Example, thus demonstrating that the DNA structures had unique properties representing new forms of DNA. Considering that fish in the Duwamish River are prone to liver tumors the distinctly different forms of DNA found in the DUW95 and DUW93 groups likely constitute critical stages in the progression to cancer.

This Example has shown that damage to the DNA of English sole exposed to environmental chemicals leads to new, diverse forms of DNA. These new forms may play a pivotal role in carcinogenesis and ultimately contribute to the development of liver cancer in the fish population. In addition, the results raise the question whether environmental chemicals play a role in generating the new forms of DNA found in breast and prostate cancers as described above.

All publications and patent applications mentioned in this specification are herein incorporated by reference to the same extent as if each individual publication or patent application was specifically and individually incorporated by reference.

From the foregoing, it will be evident that, although specific embodiments of the invention have been described herein for purposes of illustration, various modifications may be made without deviating from the spirit and scope of the invention.

I claim:

1. A method of screening for tumor progression to the metastatic state comprising the steps of:
    (a) subjecting isolated DNA or isolated nuclei to Fourier transform-infrared (FT-IR) spectroscopy to produce FT-IR spectral data;
    (b) analyzing the FT-IR spectral data of step (a) by principal components analysis (PCA); and
    (c) comparing the PCA of step (b) to the PCA of FT-IR spectra for DNA samples from non-metastatic and metastatic tumor samples.

2. A method according to claim 1 wherein the tumor is breast, urogenital, melanoma, liver, renal, pancreatic, lung, blood related, brain or colorectal cancer.

3. A method according to claim 2 wherein the urogenital cancer is prostate, ovarian or endometrial cancer.

4. A method according to claim 2 wherein the urogenital cancer is prostate cancer.

5. A method according to claim 2 wherein the tumor is breast cancer.

* * * * *